US010183007B2

(12) United States Patent
Tanaka et al.

(10) Patent No.: US 10,183,007 B2
(45) Date of Patent: Jan. 22, 2019

(54) METHOD OF PRODUCING PROANTHOCYANIDIN OLIGOMER

(71) Applicants: Nagasaki University, Nagasaki (JP); Usaien Pharmaceutical Co., Ltd., Saga (JP); Amino Up Chemical Co., Ltd., Hokkaido (JP)

(72) Inventors: Takashi Tanaka, Nagasaki (JP); Gen-ichiro Nonaka, Saga (JP); Isao Kohno, Nagasaki (JP); Hajime Fujii, Hokkaido (JP); Takashi Nakagawa, Hokkaido (JP); Hiroshi Nishioka, Hokkaido (JP)

(73) Assignees: Usien Pharmaceutical Co., Ltd., Saga-Shi, Saga (JP); Amino Up Chemical Co., Ltd., Sapporo-Shi, Hokkaido (JP); Nagasaki University, Nagasaki (JP)

( * ) Notice: Subject to any disclaimer, the term of this patent is extended or adjusted under 35 U.S.C. 154(b) by 456 days.

(21) Appl. No.: 14/976,645

(22) Filed: Dec. 21, 2015

(65) Prior Publication Data

US 2016/0151329 A1 Jun. 2, 2016

Related U.S. Application Data

(62) Division of application No. 11/814,922, filed as application No. PCT/JP2006/303402 on Feb. 24, 2006, now abandoned.

(30) Foreign Application Priority Data

Feb. 25, 2005 (JP) ................................. 2005-051070

(51) Int. Cl.
*A61K 36/00* (2006.01)
*A61K 31/353* (2006.01)
*A61K 8/49* (2006.01)
*A61K 36/04* (2006.01)
*A61K 36/14* (2006.01)
*A61K 36/15* (2006.01)
*A61K 36/185* (2006.01)
*A61K 36/485* (2006.01)
*A61K 36/54* (2006.01)
*A61K 36/61* (2006.01)
*A61K 36/73* (2006.01)
*A61K 36/734* (2006.01)
*A61K 36/74* (2006.01)
*A61K 36/77* (2006.01)
*A61K 36/82* (2006.01)
*A61K 36/87* (2006.01)
*A61K 36/88* (2006.01)
*A61K 36/889* (2006.01)
*A61Q 19/08* (2006.01)
*C07D 311/62* (2006.01)
*A61K 36/45* (2006.01)

(52) U.S. Cl.
CPC ............ *A61K 31/353* (2013.01); *A61K 8/498* (2013.01); *A61K 36/04* (2013.01); *A61K 36/14* (2013.01); *A61K 36/15* (2013.01); *A61K 36/185* (2013.01); *A61K 36/45* (2013.01); *A61K 36/485* (2013.01); *A61K 36/54* (2013.01); *A61K 36/61* (2013.01); *A61K 36/73* (2013.01); *A61K 36/734* (2013.01); *A61K 36/74* (2013.01); *A61K 36/77* (2013.01); *A61K 36/82* (2013.01); *A61K 36/87* (2013.01); *A61K 36/88* (2013.01); *A61K 36/889* (2013.01); *A61Q 19/08* (2013.01); *C07D 311/62* (2013.01); *A61K 2800/522* (2013.01)

(58) Field of Classification Search
CPC ...................................................... A61K 36/00
See application file for complete search history.

(56) References Cited

FOREIGN PATENT DOCUMENTS

| EP | 1524270 A1 | 4/2005 |
|---|---|---|
| JP | 60120818 A | 6/1985 |
| JP | 06-049053 | 2/1994 |

(Continued)

OTHER PUBLICATIONS

J.P. Steynberg, et al.; "The first condensed tannins based on a stilbene," Tetrahedron Letters, (1983), vol. 24, No. 38, pp. 4147-4150. Permagon Press, Great Britain.

(Continued)

*Primary Examiner* — Qiuwen Mi
(74) *Attorney, Agent, or Firm* — Allen Dyer Doppelt & Gilchrist

(57) ABSTRACT

The present invention relates to a composition containing as its main component proanthocyanidin oligomer to which a substance having a phloroglucinol ring structure or resorcinol ring structure has been bonded and reduced in the molecular weight, which is obtained by heating plant materials containing proanthocyanidin polymer or extract thereof with a substance having a phloroglucinol ring structure or resorcinol ring structure in an acidic aqueous solution, production method thereof, and uses of the composition in health products and pharmaceutical products. According to the invention, proanthocyanidin oligomer having physiological activity, to which a substance having a phloroglucinol ring structure or resorcinol ring structure has been bonded and reduced in the molecular weight to such a level that the oligomer can be absorbed into living body, which has been conventionally difficult to obtain at high yield from plant raw materials, can be produced efficiently and easily.

11 Claims, 9 Drawing Sheets

(56) References Cited

FOREIGN PATENT DOCUMENTS

| KR | 2001014749 A | * | 2/2001 |
|---|---|---|---|
| WO | WO 1997/36497 | | 10/1997 |
| WO | WO 200064883 | | 11/2000 |
| WO | WO 200105397 | | 1/2001 |
| WO | WO 2003091237 | | 11/2003 |
| WO | WO 2004103988 | | 12/2004 |
| WO | WO 2006090830 | | 8/2006 |

OTHER PUBLICATIONS

L. Y. Foo, et al.; "Procyanidin polymers of douglas fir bark: structure from degradation with phloroglucinol. Phytochemistry," (1989), vol. 28, No. 11, pp. 3185-3190. Pergamon Press, Great Britain.
G. M. Polya, et al.; "Inhibition of eukaryote signal-regulated protein kinases by plant-derived catechin-related compounds." Phytochemistry, (1994), vol. 35, No. 6, pp. 1399-1405. Pergamon/Elsivier, Great Britain.
L.Y. Foo, et al.; "Proanthocyanidins from lotus corniculatus." Phytochemistry, (1996), vol. 41, No. 2, pp. 617-624. Pergamon/Elsivier, Great Britain.
T. Goto, et al.; "Simultaneous analysis of individual catechins and caffeine in green tea." Journal of Chromatography A, 749 (1996), pp. 295-299. Elsevier B.V.
E. Le Roux, et al.; "A-type proanthocyanidins from pericarp of litchi chinensis." Phytochemistry, (1998), vol. 48, No. 1, pp. 1251-1258. Pergamon/Elsivier, Great Britain.
N. Taylor; "Green tea." Kensington Books (1998), p. 152. New York, USA.
L.Y. Foo, et al.; "Isolation and identification of procyanidins in apple pomace." Food Chemistry 64, (1999), pp. 511-518. Elsevier.
L.Y. Foo, et al.; "The structure of cranberry proanthocyanidins which inhibit adherence of uropathogenic P-fimbriated *Escherichia coli* in vitro." Phytochemistry 54 (2000), pp. 173-181. Pergamon/Elsevier.
P. Sarni-Manchado, et al.; "Phenolic composition of litchi fruit pericarp." J. Agric. Food Chem. 48 (2000), pp. 5995-6002.
J.A. Kennedy, et al.; "Analysis of proanthocyanidin cleavage products following acid-catalysis in the presence of excess phloroglucinol." J. Agric. Food Chem. 49 (2001), pp. 1740-1746.
K. Waseem, et al.; "Effect of fruit orientation on the quality of litchi (Litchi chinenesis Sonn) under the agro-climatic conditions of Dera Ismail Khan-Pakistan." International Journal of Agriculture & Biology (2002), vol. 4, No. 4, pp. 503-505.
F. Hashimoto, et al., "Evaluation of the anti-oxidative effect (in vitro) of tea polyphenols." Biosci. Biotechnol. Biochem., 67 (2) (2003), pp. 396-401.
S. Rosenthal, "The Gynecological Sourcebook." McGraw-Hill Professional. (2003), pp. 22.
J. Harder, "Green Tea." Restaurant Business, vol. 102, Issue 19, (Nov. 15, 2003), pp. 50-52. (pp. 1-3 of EBSCOhost).
M.A. Rao, et al.; "Engineering Properties of Foods." CRC Press (2005), pp. 185.
B.K. Kubata, et al., "Kola acuminata proanthocyanidins: a class of anti-trypanosomal compounds effective against Trypanosoma brucei." International Journal for Parasitology 35 (2005), pp. 91-103. Elsevier.
A. B. Howell, et al.; "A-type cranberry proanthocyanidin and uropathogenic bacterial anti-adhesion activity." Phytochemistry, 66 (2005), pp. 2281-2291. Elsevier.
R.O. Young, et al.; "The pH Miracle for Weight Loss: Balance Your Body Chemistry, Achieve Your Ideal Body Weight." Hachette Digital, Inc. (2005), 1 page (not numbered).
Jack Eden; Common pH Values. Retrieved from the internet, <http://www.jackeden.com/tips/phmat.html>. Retrieved on Feb. 3, 2011. 1 page.
European Patent Office Search Report; European Search Report dated Sep. 11, 2014; 3 pages.

* cited by examiner

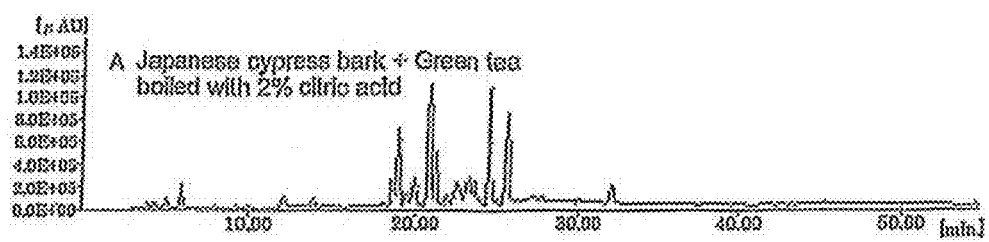
Fig1A
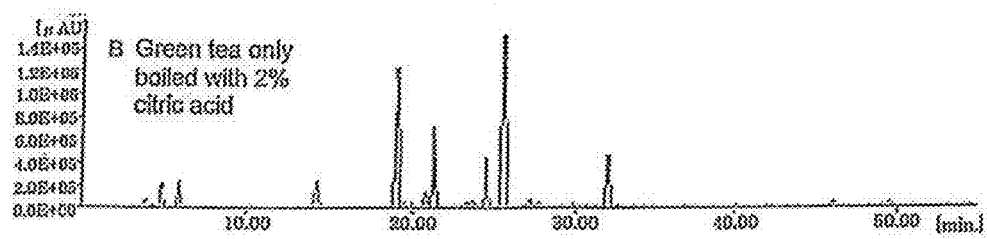
Fig1B
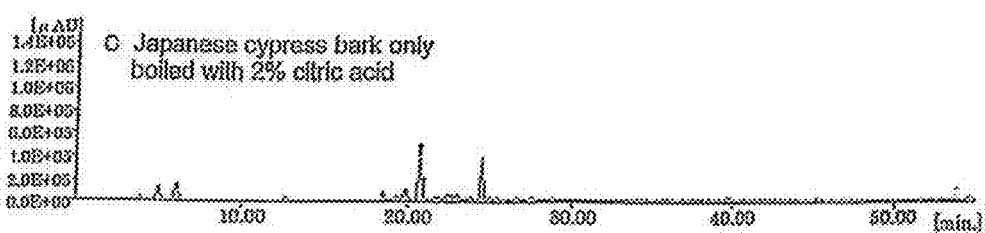
Fig1C
Fig2
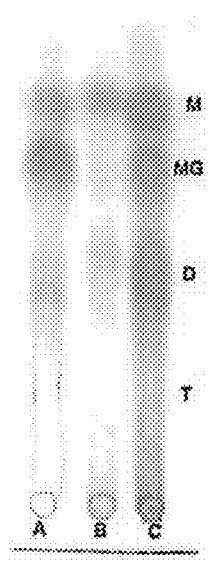

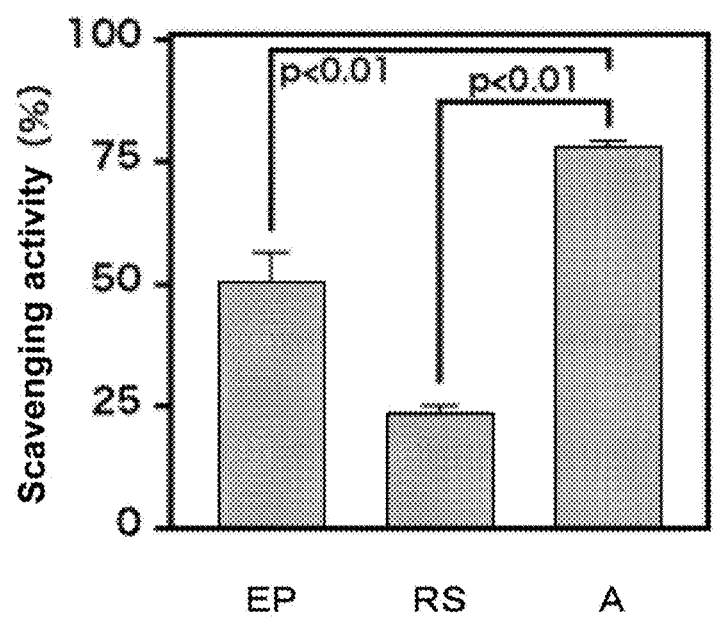

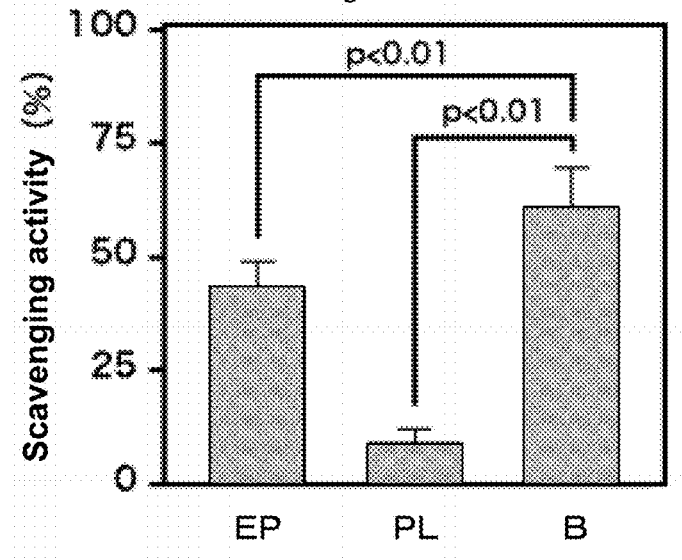
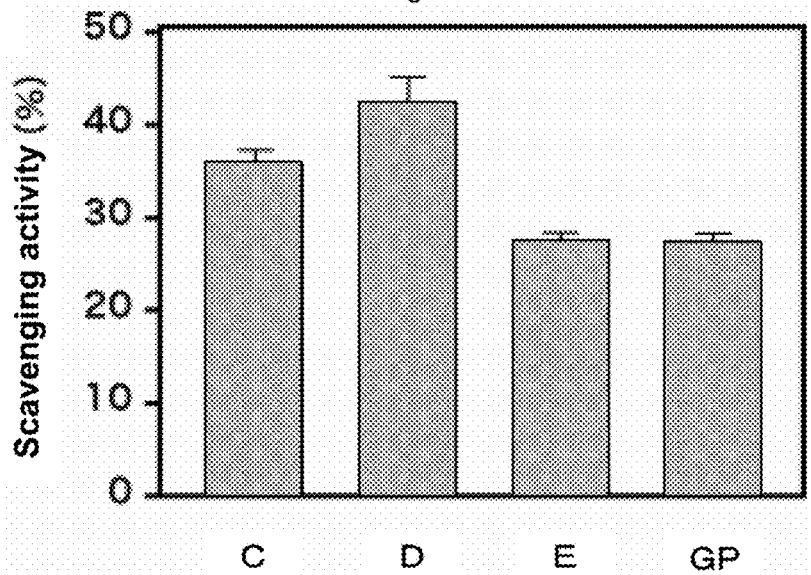

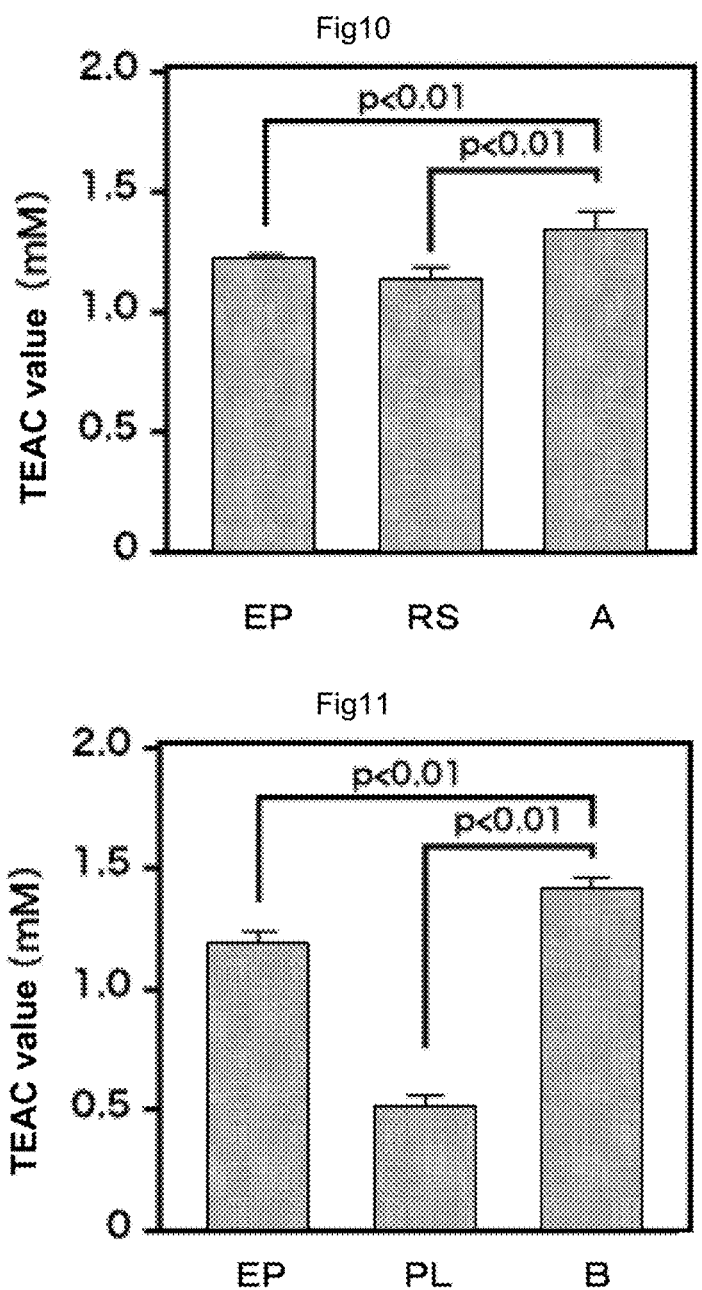

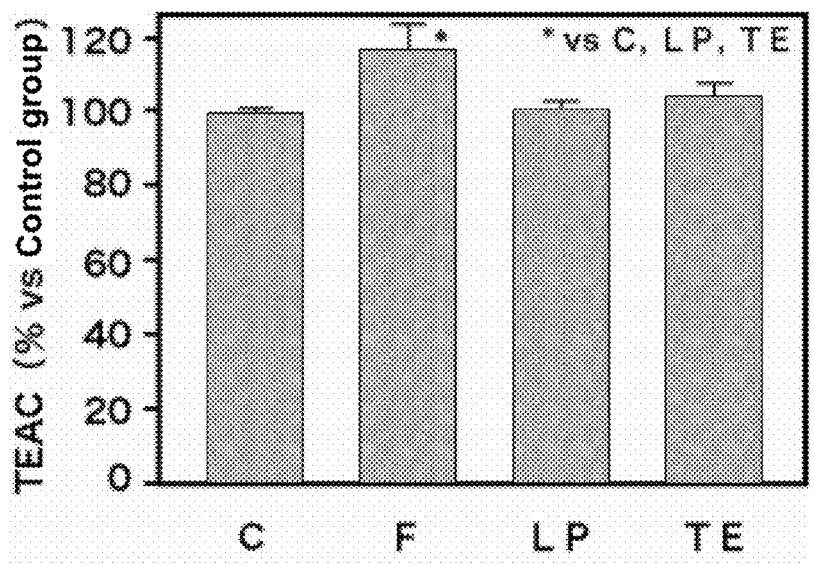
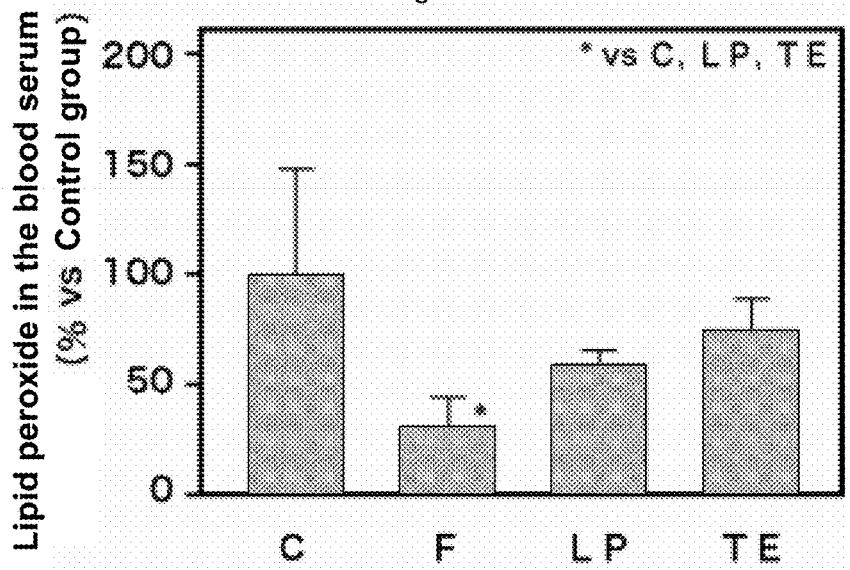

METHOD OF PRODUCING PROANTHOCYANIDIN OLIGOMER

CROSS-REFERENCE TO RELATED APPLICATION

This application is a divisional of U.S. patent application Ser. No. 11/814,922 filed on Jul. 27, 2007, which is the § 371 National Stage of International Application No. PCT/JP2006/303402, filed on Feb. 24, 2006, the contents of which applications are herein incorporated by reference in their entirety.

FIELD OF THE INVENTION

This invention relates to a method of producing a proanthocyanidin oligomer, which can reduce a molecular weight of proanthocyanidin polymer in plant to a level that it can be absorbed (easily by the gastrointestinal tract) into a living body.

More specifically, the invention relates to a composition containing proanthocyanidin oligomer having a polymerization degree of 2 to 4 and having a phloroglucinol ring structure or resorcinol ring structure bonded at its terminal, which is obtained by heating a material containing proanthocyanidin polymer together with a substance having a phloroglucinol ring structure or resorcinol ring structure in an acidic solution, a production method thereof, uses of the composition and a novel proanthocyanidin oligomer having a phloroglucinol ring structure or resorcinol ring structure bonded thereto.

BACKGROUND OF THE INVENTION

The composition containing proanthocyanidin oligomer obtained according to the invention can be used in food products, health food products, foods for specified health use, cosmetic products and medical products. Especially, the composition is useful as composition for health food products and medical products for prevention of lifestyle-related diseases caused by generation of reactive oxygen species, prevention and treatment of brain diseases or prevention of aging.

Owing to excessive fat intake due to changes in our eating habits, increased exposure to UV rays due to changing environment, ozone depletion and the like, increase in environmental pollutants and the like, incidence rates of so-called lifestyle-related diseases such as hyperlipemia, hypercholesteremia, high pressure, diabetes and cancers are increasing and the number of patients with allergies or with brain diseases such as dementia is also increasing. There is concern that the number of patients with dementia or Alzheimer's syndromes will be increasing in the future with rapid aging of the society. Involvement of reactive oxygen species generated in vivo has been pointed out as factors contributing to these diseases. (Bioorganic & Medicinal Chemistry, Vol. 10 (2002), p.p. 2497-2509, Non-Patent Document 1). However, since perfect technology for suppressing or controlling generation of reactive oxygen species has not been developed yet, there has not been established a sufficiently sure medical technology useful for treating and preventing lifestyle-related diseases, brain diseases and the like.

Recently, natural substances present in plants and exhibiting physiological activities, especially, compounds of polyphenols have been attracting attentions. Polyphenols, which are generally contained in teas, vegetables, fruits, herbs and the like, can be expected to be ingested as food and beverages for a long period of time and serve as treatment/prevention agent free of side effects.

Polyphenol compounds, plant secondary metabolites, which universally exist in the plant world in large quantity and are known to exhibit various physiological activities, attracted attention in the fields of pharmaceuticals and phytochemistry in old times and recently have been drawing attention in the field of health food. For example, tea polyphenols, especially catechins are known to have a wide range of physiological activities such as antibiotic properties, antiviral action, antimutagenic property, antioxidation effect, blood-pressure increase suppression, property of reducing cholesterol in the blood, antidecay property, antiallergic activity, improvement of enteric flora, odor eliminating activity and the like.

Among polyphenols, proanthocyanidins are contained in a wider range of plants. In order for proanthocyanidins to exhibit various physiological activities, proanthocyanidin compound needs to be absorbed into the living body by the gastrointestinal tract. However, molecular weights of proanthocyanidins are generally said to be on the order of several thousands to several tens of thousands. Substance having such a large molecular weight is difficult to be absorbed by the gastrointestinal tract and in many cases, even if it is ingested, it is not absorbed in the living body and not used as nutrition.

The term "proanthocyanidins", is a generic name for procyanidin, prodelphinidin, propelargonidin and the like of polymers of dimer, trimer, tetramer, decamer or higher oligomers having as constituent unit flavan-3-ol (also referred to as catechins) and those with gallic acid esterified thereto, and stereoisomers thereof, which are polyphenol compounds generating anthocyanidins through acid treatment. The constituent units are bonded to each other through carbon-carbon bond between the 4-position and 8-position of the carbon skeleton or between the 4-position and 6-position, or sometimes through ether bond between the 2-position and 7-position in addition to the carbon-carbon bond.

Proanthocyanidin has an excellent antioxidative effect (Arch. Biochem. Biophys., Vol. 374, p.p. 347-355, 2000: Non-Patent Document 2), and moreover, since it has other effects such as improvement of blood flow, antistress action, antihypertensive efficacy, antibiotic effect, antitumor effect, anticataract activity and antidiarrheic effect, it has been used as a naturally-derived substance having a health-maintaining effect.

Proanthocyanidins are isolated as mixture from pine bark, immature apple fruit, grape seeds and the like and now, are blended in beverages, confectioneries, health foods, cosmetic products, hair-growth drugs and the like which are commercially available.

In many plants containing proanthocyanidin, various proanthocyanidins from those having a low polymerization degree to those having a high molecular weight are contained as mixture, and many of them are plants mainly containing proanthocyanidins of high polymerization degree such as persimmon, banana and Chinese quince. However, among proanthocyanidins, a proanthocyanidin polymer having a high polymerization degree is said to be inferior in pharmacological activities to proanthocyanidin oligomers having polymerization degree of 2 to 4 due to its poorabsorbability from the intestine. Also, it is preferable that such a proanthocyanidin polymer, having strong astringency and poor solubility in water, be eliminated when the plant is used in food products (Free Radical Res., Vol. 29, p.p. 351-358, 1998: Non-Patent Document 3). Based on these facts, proanthocyanidin oligomer having a polymerization degree of 2 to 4 have been attracting attention as having excellent health-maintaining effect and those derived from pine bark are used in beverages and health foods.

In order to obtain only proanthocyanidin from plant extract, absorption method (see, for example, H06-49053: Patent Document 1) and the like are employed. But it is difficult to isolate those different in polymerization degrees. In order to obtain only proanthocyanidin oligomers of polymerization degree 2 to 4, solvent partition method using ethyl acetate, solid-phase extraction method with methyl acetate and chromatography method (PCT Publication WO00/64883: Patent Document 2), chitin absorption method (PCT Publication WO03/091237: Patent Document 3) and the like are employed for isolate only low molecular weight proanthocyanidins through extraction. However, in these methods, a large amount of high molecular weight proanthocyanidin polymers is discarded, which is disadvantageous in terms of yield.

As an alternative method replacing the methods isolating proanthocyanidin oligomers of polymerization degree 2 to 4 from plants containing proanthocyanidin polymers, the present inventors previously proposed a method of reacting proanthocyanidin polymer-containing material with SH-containing compound such as cysteine in an acidic solution to reduce the molecular weight of the proanthocyanidin oligomer (PCT Publication WO2004/103988: Patent Document 4). According to the method, proanthocyanidin oligomer having the cysteine bonded thereto to thereby reduce the molecular weight and be excellent in systemic absorption can be obtained. It has been confirmed that the proanthocyanidin oligomer has no toxicity and can be used safely. However, at present, in some countries (including Japan), there is a problem that strict procedures are required for obtaining approval of uses of health food products containing proanthocyanidin having cysteine attached thereto which is non-natural chemical substance.

[Patent Document 1] Japanese Patent Application Laid-Open No. H06-49053.
[Patent Document 2] PCT Publication No. WO00/64883
[Patent Document 3] PCT Publication No. WO03/091237
[Patent Document 4] PCT Publication No. WO2004/103988
[Non-Patent Document 1] Bioorganic & Medicinal Chemistry, Vol. 10 (2002), p.p. 2497-2509
[Non-Patent Document 2] Arch. Biochem. Biophys., Vol. 374, p.p. 347-355, 2000
[Non-Patent Document 3] Free Radical Res., Vol. 29, p.p. 351-358, 1998

SUMMARY OF THE INVENTION

The object of the invention is to provide a convenient and efficient method for reducing molecular weight of proanthocyanidin oligomer, being widely distributed in nature as proanthocyanidin polymer but limited in naturally-derived materials as oligomer, by using as starting material proanthocyanidin polymer, plant containing proanthocyanidin polymer or extract thereof and bonding the material to a substance having a phloroglucinol ring structure or resorcinol ring structure.

With a view to achieving the above object, the inventors have made intensive studies and as a result, have found that proanthocyanidin can be fractionated and reduced in its molecular weight and at the same time can be converted into proanthocyanidin oligomer having catechin bonded thereto at terminal by gently boiling fruit, fruit skin, bark, leaves or extract thereof containing proanthocyanidin polymer such as date plum, banana, grape, pine, *Chamaecyparis* obtuse, camphor tree, wax myrtle, Chinese quince, litchee, *Myrica rubra* and *Cinnamomi* Cortex together with green tea or fresh tea leaves containing a large amount of low-molecular weight catechins in an acidic solution for 2 to 3 hours.

Further, the inventors have found that proanthocyanidin can be fractionated, reduced in its molecular weight and converted into proanthocyanidin oligomer having a substance having a phloroglucinol ring structure or resorcinol ring structure bonded thereto by using the substance having a phloroglucinol ring structure or resorcinol ring structure and other plant materials (such as grape seed and grape skin) containing such a substance instead of green tea or fresh tea leaves, and have completed the invention based on the findings.

That is, the invention relates to the following 1 to 14 items, a composition containing as its main component proanthocyanidin oligomer to terminal of which a substance having a phloroglucinol ring structure or resorcinol ring structure is bonded by heating a plant containing proanthocyanidin polymer or extract thereof with green tea or fresh tea leaves in an acidic aqueous solution (1 to 5). Production method thereof (6 to 9), uses of the composition (10 to 12) and a novel proanthocyanidin oligomer (13 to 14).

1. A composition containing as its main component proanthocyanidin oligomer to terminal of which a substance having a phloroglucinol ring structure or resorcinol ring structure has been bonded and reduced in the molecular weight, which is obtained by heating plant materials containing proanthocyanidin polymer or extract thereof with a substance having a phloroglucinol ring structure or resorcinol ring structure, plant containing such a substance or extract thereof in an acidic aqueous solution.

2. The composition containing as its main component proanthocyanidin oligomer described in 1, wherein the plant containing proanthocyanidin polymer is at least one kind selected from a group consisting of grape, pine, *Chamaecyparis* obtuse, camphor tree, wax myrtle, cacao, date plum, banana, Chinese quince, apple, hawthorn, litchee, *Myrica rubra* and *Cinnamomi* Cortex.

3. The composition containing as its main component proanthocyanidin oligomer described in 1, wherein the substance having a phloroglucinol ring structure or resorcinol ring structure is at least one kind selected from a group consisting of resveratrol, phloroglucinol, flavonoid and flavanoid (galloylester of catechin).

4. The composition containing as its main component proanthocyanidin oligomer described in 1, wherein the substance having a phloroglucinol ring structure or resorcinol ring structure is at least one kind selected from a group consisting of green tea, fresh tea leaves, grape seed, grape seed coat, cube gambir, red algae and extracts thereof.

5. The composition containing as its main component proanthocyanidin oligomer described in 1, having a polymerization degree of 2 to 4.

6. A method for producing the composition containing as its main component proanthocyanidin oligomer described in any one of 1 to 5, comprising a step of heating plant materials containing proanthocyanidin polymer or extract thereof with plants having a phloroglucinol ring structure or resorcinol ring structure or extract thereof in an acidic aqueous solution and a step of concentrating the reaction solution containing proanthocyanidin oligomer having a phloroglucinol ring structure or resorcinol ring structure bonded to the terminals and reduced in the molecular weight and drying the solution.

7. A method for producing the composition containing as its main component proanthocyanidin oligomer described in any one of 1 to 5, comprising a step of concentrating the reaction solution containing proanthocyanidin oligomer having a substance having a phloroglucinol ring structure or resorcinol ring structure bonded at the terminals and reduced in the molecular weight and a step of subjecting the concentrated solution to fractionating treatment.

8. The method for producing a composition containing as its main component proanthocyanidin oligomer described in 6 or 7, wherein the acidic condition is prepared by using an inorganic acid, organic acid or both of the two.

9. The method for producing a composition containing as its main component proanthocyanidin oligomer described in 8, wherein at least one kind selected from the group consisting of hydrochloric acid, sulfuric acid, nitric acid, acetic acid, citric acid, ascorbic acid and malic acid.

10. The composition containing proanthocyanidin oligomer described in any one of 1 to 5, used in health food products for treatment/prevention of lifestyle-related diseases caused by generation of reactive oxygen species and brain diseases or for prevention of aging.

11. The composition containing proanthocyanidin oligomer described in 10, used in pharmaceutical products for treatment/prevention of lifestyle-related diseases caused by generation of reactive oxygen species and brain diseases or for prevention of aging.

12. The composition containing proanthocyanidin oligomer described in 10, used in cosmetic products for prevention of aging caused by generation of reactive oxygen species.

13. A proanthocyanidin oligomer represented by formula (1) below.

[Chem. 1]

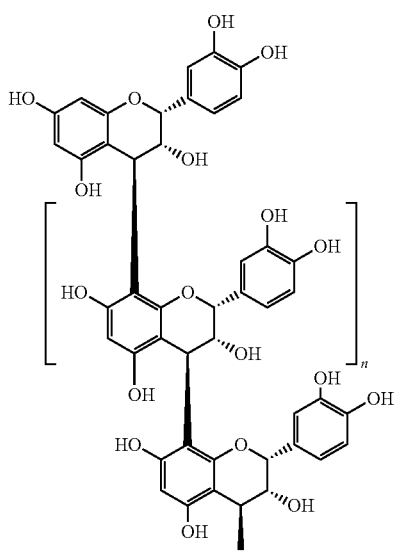

(1)

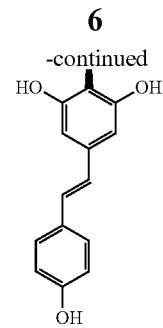

(In the formula, n is 0 or an integer of 1 to 2.)

14. A proanthocyanidin oligomer represented by formula (2) below.

[Chem.2]

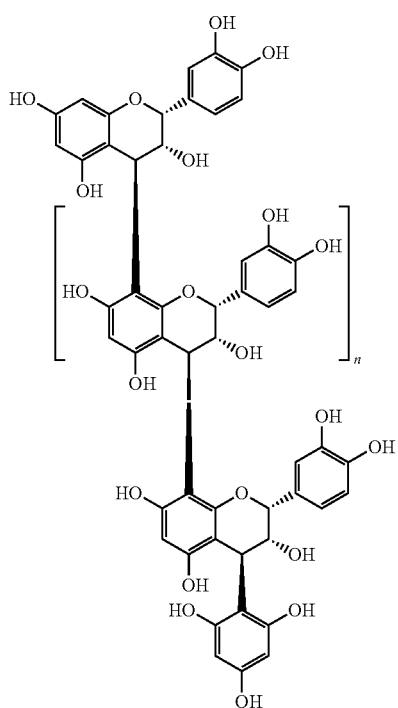

(2)

(In the formula, n is 0 or an integer of 1 to 2.)

Effect of Invention

The invention provides a method for producing a composition containing as its main component proanthocyanidin oligomer to which a substance having phloroglucinol ring structure or resorcinol ring structure has been bonded at the terminals and which thereby has been reduced in the molecular weight, which composition is obtained by concentrating and drying a reaction solution obtained by heating plant materials containing proanthocyanidin polymer or extract thereof with a substance or plants having a phloroglucinol ring structure or resorcinol ring structure or extract thereof in an acidic aqueous solution. According to the invention, proanthocyanidin oligomer, to which a substance having phloroglucinol ring structure or resorcinol ring structure has been bonded at the terminals and which thereby has been reduced in the molecular weight, and which is useful as composition for health food products and pharmaceutical products for treatment/prevention of lifestyle-related diseases caused by generation of reactive oxygen species and brain diseases or for prevention of aging, can be efficiently produced from proanthocyanidin polymer-containing materials.

DETAILED DESCRIPTION OF THE PREFERRED EMBODIMENTS

Raw materials used for producing proanthocyanidin oligomer according to the method of the invention are proanthocyanidin polymer-containing plants (such as fruit, fruit skin, bark and leaves) or extracts thereof.

Here, examples of proanthocyanidin polymer-containing plants include fruit vegetables such as astringent persimmon, banana, apple, pear, grape, strawberry, *persea americana*, blueberry, hawthorn, lotus root, buckwheat, litchee and *Myrica rubra*, herbs, spices, wood, *Cinnamomi* Cortex and pine balk. Among these, astringent persimmon, banana, grape, pine, *Chamaecyparis obtusa*, camphor tree, wax myrtle, Chinese quince, litchee and *Myrica rubra* are preferably used.

In the invention, these plants containing proanthocyanidin polymer are chopped (cut) or crushed and then used and extracts obtained by heating and concentrating/drying these materials in aqueous solvent are used.

There is no particular limitation on the substance having phloroglucinol ring structure or resorcinol ring structure used in the reaction of the present invention as long as the substance is a plant containing resveratrol, phloroglucinol, flavonoid and flavanoid (galloylester of catechin) or extracts thereof. Examples thereof include green tea, fresh tea leaves, grape seed, grape seed coat, cube gambir, red algae and extracts thereof. Among these, in consideration that the main uses of the proanthocyanidin oligomer produced in the present invention is health food products, ingredient for food for specified health use, cosmetic products and pharmaceutical products, especially food for specified health use and pharmaceutical products, grape seed, grape seed coat, green tea, fresh tea leaves and extracts thereof, which have been conventionally applied to drinking and safety of which has been confirmed, are preferred.

The proportion of proanthocyanidin polymer-containing plant materials and substance having phloroglucinol ring structure or resorcinol ring structure used in the reaction is arbitrarily selected. It is preferred that the amount of the latter be large enough to bond to the fragments of the proanthocyanidin polymer having reduced in the molecular weight. If the amount of the substance having phloroglucinol ring structure or resorcinol ring structure is too small, proanthocyanidin having a high molecular weight may remain unreacted, and in that case, the remaining proanthocyanidin having a high molecular weight can be easily removed by column chromatography.

Reaction between plant containing proanthocyanidins or proanthocyanidins contained in extract thereof and the substance having phloroglucinol ring structure or resorcinol ring structure (hereinafter, sometimes simply referred to as "phloro/resorcinol ring-containing substance") is conducted in solvent by heating.

As reaction solvent, water, methanol, ethanol and a mixture of two or more of them is used. In consideration that the product is used in food or pharmaceutical products, water and ethanol are preferred.

It is preferred that the reaction be carried out under an acidic condition. An acid appropriately selected from inorganic acids such as hydrochloric acid, sulfuric acid and nitric acid and organic acids such as acetic acid, citric acid, ascorbic acid and malic acid is used in a concentration of 0.1 to 1.0 N, preferably about 0.5 N.

Reaction between plant or plant extract containing proanthocyanidins and phloro/resorcinol ring-containing substance is carried out at a temperature of room temperature to 100° C. for 0.5 hours to 1 week, preferably at 90 to 100° C. for 1 to 4 hours.

The reaction solution after the reaction is subject to filtration or the like treatment to thereby remove solid content and isolate the liquid. The resultant extract (liquid) containing proanthocyanidin oligomer can be used in various forms such as liquid, powder, gel, solid molded product or the like after condensed and dried. The reaction solution after the reaction may be concentrated and dried or concentrated and fractionated. By these methods, the target substance is separated from the reaction solution, concentrated and purified by conventional method. For, example, residues are separated by filtration and after the filtrate is concentrated, the concentrated liquid can be purified by subjecting the extract to film treatment (such as ultrafiltration and reverse osmosis treatment) or to treatment with adsorbent or the like treatment to thereby concentrate and isolate the target substance.

Examples of adsorbents include styrene-divinylbenzene adsorbent, methacrylic acid adsorbent, hydrophilic vinyl polymer, modified dextran gel, polyacrylamide gel, reverse-phase silica gel and ion-exchange resin. In a case where such an adsorbent is used, proanthocyanidin oligomers, which have been reduced in the molecular weigh through reaction with the phloro/resorcinol ring-containing substance, are contained in fraction adsorbed to the adsorbent (hereinafter, referred to as "adsorbed fraction(s)"). By eluting the adsorbed fraction with hydroalcohol, alcohol, acetone or the like, components having various molecular weights can be obtained. On this occasion, by isolating the target proanthocyanidin oligomer having a polymerization degree of 2 to 4 from the reaction solution through column chromatography using aromatic compound-based synthetic adsorbent, proanthocyanidin having a high molecular weight can be sifted out and concentration of the eluate is easy, which is preferred. Preferred examples of aromatic compound-based synthetic adsorbent include cross-linked styrene-based porous polymer such as SEPABEADS.

By results of measurements using $^1$H-NMR, UV, HPLC, GPC and TLC, it is confirmed that the thus-obtained proanthocyanidin oligomer contains dimers to tetramers of proanthocyanidin whose typical chemical structure is represented by formulae (1) and (2).

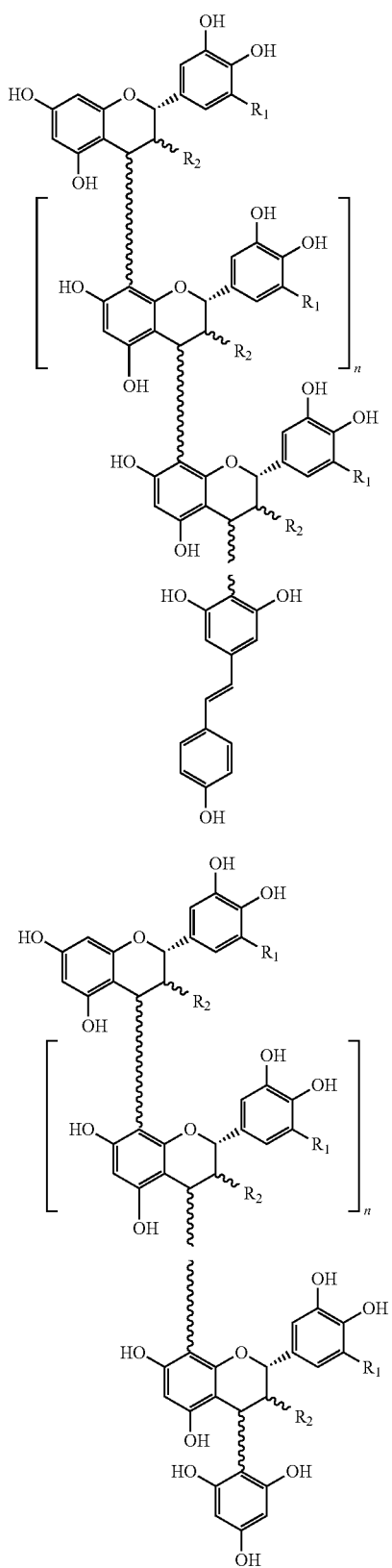

(1)

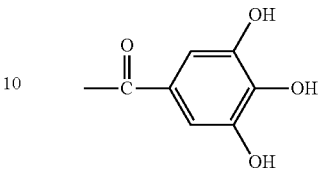

(2)

(In the formula, $R_1$ represents a hydrogen atom or a hydroxyl group, and $R_2$ represents a hydrogen atom or a hydroxyl group, $R_2$ represents a hydrogen atom or a galloyl group,

[Chem. 4]

and n represents 0 or an integer of 1 to 2.)

Although in formulae (1) and (2), only structures having bonded between 4 position and 8 position are shown, those having bonding between 4 position and 6 position or bonding of 2-O-7 also exist.

Through reaction between proanthocyanidin polymer and phloro/resorcinol ring-containing substance according to the invention, proanthocyanidin polymer having a high molecular weight (5 in terms of polymerization degree) and not absorbable into living body can be easily fragmented to thereby render the polymer a low molecular weight substance absorbable and at the same time, a composition mainly containing proanthocyanidin oligomers of dimer to tetramer can be obtained.

The proanthocyanidin oligomer having a phloro/resorcinol ring structure-containing substance bonded to its terminal, obtained according to the invention, which exhibits strong antioxidative activity in DPPH, TEAC and FRAP antioxidation tests, has high antioxidative function as compared with other polyphenol materials. Further, in animal experiments regarding lifestyle-related diseases and monitoring tests antioxidation index on humans, data evidencing that the effect can be judged to be based on antioxidative activity have been obtained.

Accordingly, products containing the proanthocyanidin oligomer of the invention as active ingredient have not only an action to suppress generation of lipid peroxide in vivo but also effects on diseases caused by oxidative induced due to active oxygen. Therefore, the products, which have effects of preventing various organ failures caused by generation of lipid peroxide or active oxygen and also preventing aging, are effective in preventing and treating various diseases caused by such organ failures and aging. Moreover, the products can be considered to be effective in suppressing/preventing/treating cerebral dysfunctions such as dementia presumably caused by brain aging. At the same time, along with improvement in brain functions, enhancement in learning function, easing irritation, relieving insomnia, easing disconcertedness and the like effects can be expected. Thus, products containing proanthocyanidin oligomer of the invention as active ingredient can be used in health food products, pharmaceutical products, cosmetics and the like.

No toxicity is observed with products containing proanthocyanidin oligomer of the invention as active ingredient and the products can be used safely. These products are used orally or parenterally. The dosage amount in a case of oral use differs depending on the age, weight, symptoms, target therapeutic effect, administration method and the like. Generally, it is in a range of 50 to 1000 mg per dose for adults.

In case of oral administration, products of the invention are used in form of tablet, ball, capsule, powder, granulated powder, syrup and the like. In case of parenteral administration, they are used in form of injectable solution, coating agent and the like. In case of preparing granulated products, tablet products or syrup products, appropriate auxiliary agents (such as starches, dextrin, sweetening agents, colorants and flavoring agents) can be used.

Hereinafter, the invention is described specifically by referring to Examples. The invention is by no means limited by the Examples.

Example 1

[Chem. 5]

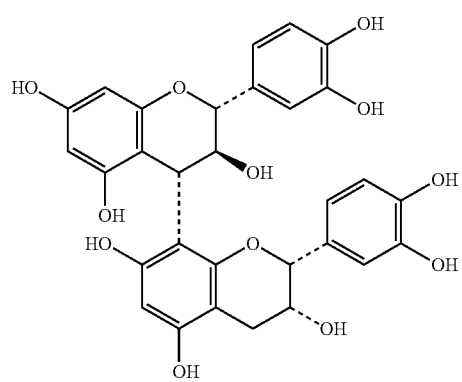

Procyanidin B4

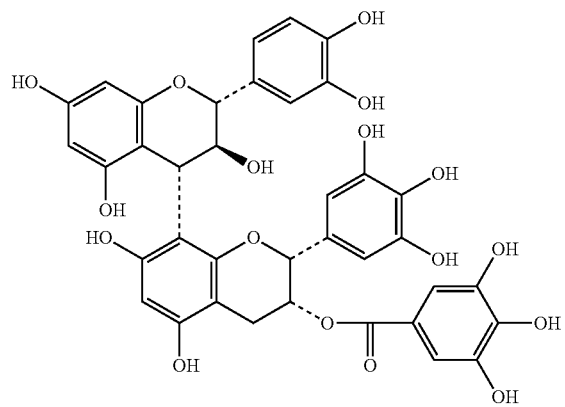

(+)-catechin (4β-8)-(-)-epigallocatechin 3-O-gallate

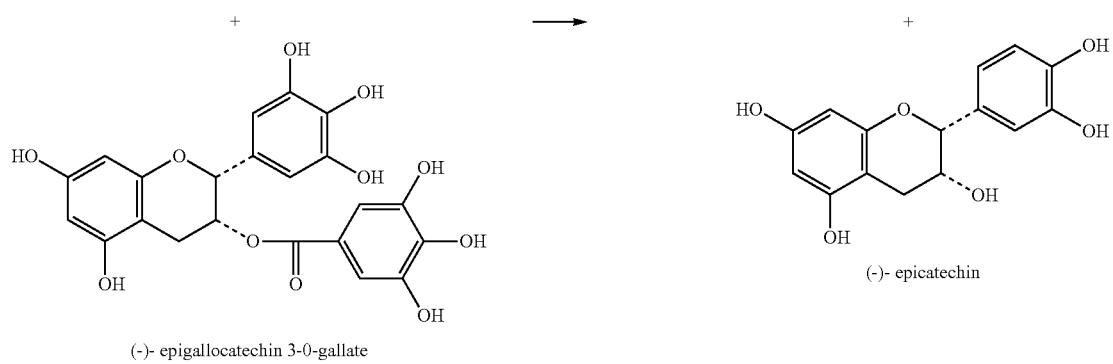

(-)- epigallocatechin 3-O-gallate (-)- epicatechin

Procyanidin B4 (100 mg) and epigallocatechin 3-O-gallate (100 mg) were dissolved in 40 mL of 2% citric acid solution and heated at 100° C. for 2 hours. After cooled down, the reaction solution was subjected to MCI-gel CHP20P (aqueous methanol) column chromatography and then to Sephadex LH-20 (60% methanol) column chromatography, to thereby recover as raw material procyanidin B4 (10 mg) and epigallocatechin 3-O-gallate (59.2 mg) and also obtain newly generated (−)-epicatechin (25.4 mg) and (+)-catechin (4β→8)-(−)-epigallocatechin 3-O-gallate (17.3 mg). By comparing in $^1$H-NMR spectra the generated catechin and proanthocyanidin with compositions of prior art, identification of the obtained compositions was conducted. (See the above structural formulae.)

Example 2

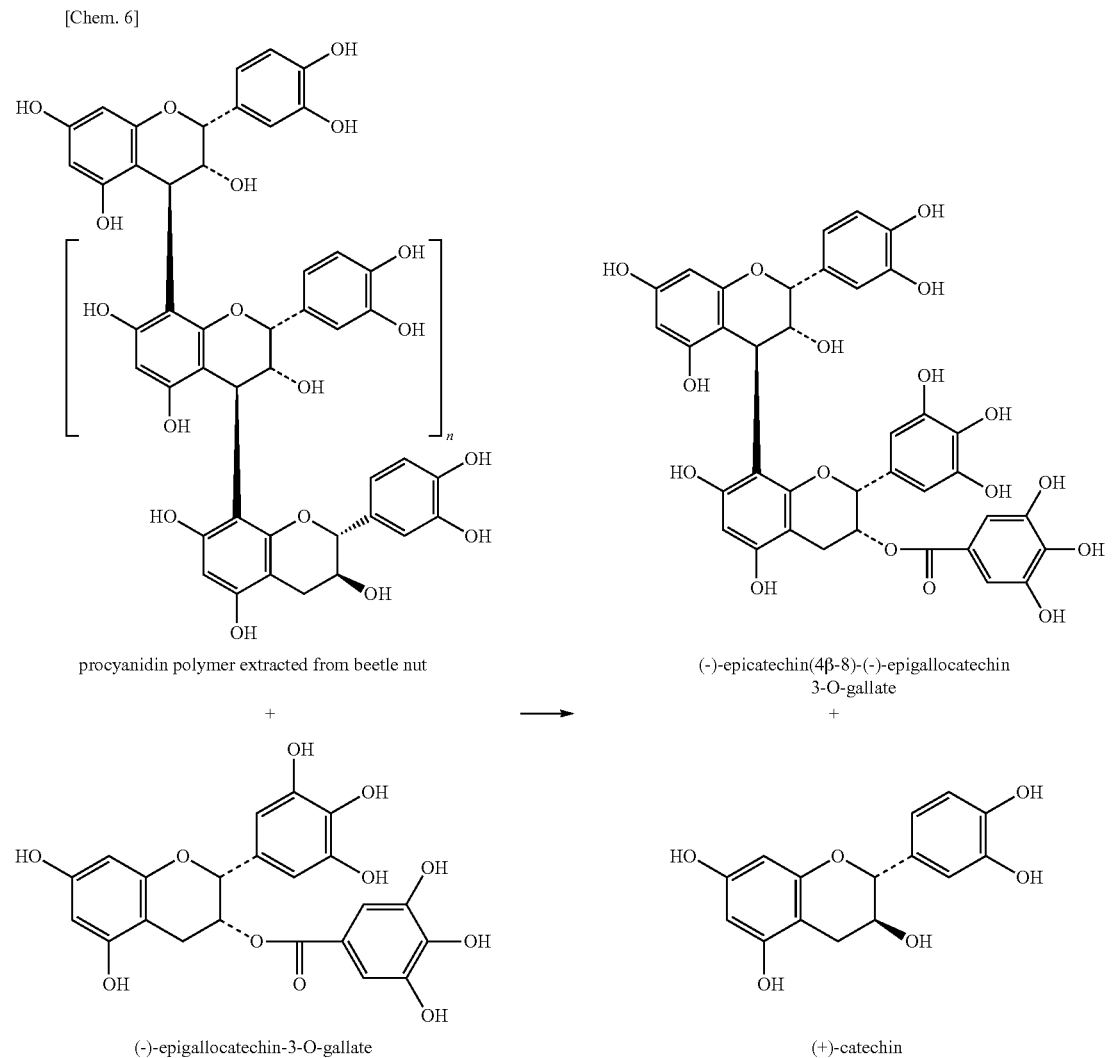

procyanidin polymer extracted from beetle nut (−)-epigallocatechin-3-O-gallate (−)-epicatechin(4β-8)-(−)-epigallocatechin 3-O-gallate (+)-catechin 0.5 g of procyanidin polymer extracted from beetle nut and (−)-epigallocatechin 3-O-gallate (0.5 g) were dissolved in 200 mL of 2% citric acid solution and heated at 95° C. for 3 hours. The reaction solution was subjected to column chromatography in the same manner as Example 1, epigallocatechin 3-O-gallate (403 mg), newly generated (+)-catechin (48.6 mg) and (−)-epicatechin (4β→8)-(−)-epigallocatechin 3-O-gallate (148.3 mg) which is proanthocyanidin were obtained (see the above structural formulae).

Example 3

5 g of Japanese cypress bark containing a mixture of catechin and procyanidin and 1 g of green tea were dissolved in 100 mL of 2% citric acid solution and heated at 95° C. for 3 hours. After cooling down, 100 mL of ethanol was added to the solution and the solution was subjected to suction filtration. The filtrate was analyzed by HPLC. The conditions for HPLC analysis were as follows.

Column: Cosmosil 5C18 ARII (4.6×250 mm),
Column temperature: 35° C.,
Mobile phase: A; 50 mM phosphoric acid,
B; $CH_3CN$,
B from 4% to 30% (for 39 minutes),
from 30 to 75% (for 15 minutes),
Flow rate: 0.8 mL/min,
Detection: Photodiode array detection 5 g of Japanese cypress bark and 1 g of green tea were separately heated in citric acid solution under the same condition and then subjected to extraction treatment. HPLC analysis was conducted in the same manner (see HPLC in FIG. 1). In the extract solution obtained by treating the mixture of Japanese cypress bark and green tea in the citric acid solution, peaks derived from many new compounds, which were not found in the cases of treating Japanese cypress bark and green tea separately, were detected. It was presumed by comparison in ultraviolet absorption spectra of the peaks between those obtained in this Example and those obtained Examples 1 and 2 that all of the compounds were proanthocyanidins.

The extract liquid obtained in Example 3 by heating Japanese cypress bark and green tea in the citric acid solution was concentrated and then subjected to solvent partition with 50 mL of water and 50 mL of ethyl acetate 5 times. The obtained ethyl acetate layer was gathered together and also concentrated to thereby obtain 0.67 g of ethyl acetate extracted product. The extracts obtained from the separately treated Japanese cypress bark and green tea respectively were subjected to solvent partition in the same manner, to thereby obtained 0.30 g of ethyl acetate extracted product from the Japanese cypress bark and 0.37 g of ethyl acetate extracted product from the green tea. The thus obtained three extracts of ethyl acetate were analyzed by TLC. The conditions of TLC are as follows.

Silica gel 60,
Developing solvent: benzene-ethyl formate-formic acid (1:7:1, v/v)
Coloring reagent: vanillin hydrochloric acid reagent (see TLC in FIG. 2.)

Vanillin hydrochloric acid reagent, which is a detection reagent for catechins and proanthocyanidins, takes on a color of characteristic red when these substances are present. With respect to the extract obtained through treatment of Japanese cypress bark and green tea in the citric acid solution, spots derived from proanthocyanidin dimmer and trimer were acknowledged.

In the water layer remaining after ethyl acetate partition in Example 3, proanthocyanidin, having a higher molecular weight than the molecular weight of those transferred to the ethyl acetate layer, remains. Then, molecular weights of acetylated compounds of proanthocyanidins contained in the water layer were compared by gel permeation chromatography analysis. The water layer after Japanese cypress bark and green tea was treated with citric acid solution and the water layer of Japanese cypress bark were concentrated and dried to be solid. After dissolved in acetic anhydride-pyridine, the solution was left standing at room temperature for 8 hours. The reaction solutions were respectively poured into ice water, and insoluble matter deposited was taken out though filtration and vacuum-dried. The obtained acetylated body was analyzed under conditions of TSK-GEL G4000H6 column, solvent of tetrahydrofuran, and detection with 254 nm UV absorption. According to molecular weight of the obtained products estimated based on calibration curves prepared by using benzene and polystyrenes having molecular weights of 4000, 25000 and 50000, the peak top of proanthocyanidin contained in the water layer after treating Japanese cypress bark and green tea with citric acid was about 1300 while the peak top of proanthocyanidin contained in the water layer of Japanese cypress bark was about 2000. It was found out that by adding green tea in the citric acid treatment, the molecular weight was reduced.

Example 4

100 g of fresh banana skin was pulverized together with 300 ml of acetone-water mixture solution (4:1, v/v) by using a whirling blender and subjected to suction filtration. Acetone was distilled off the filtrate by using an evaporator to thereby prepare an aqueous solution, insoluble matter was filtered out and water is added to the solution to make the total amount 200 ml. Separately, 3 g of green tea leaves was boiling extraction in 300 ml of water and after the resultant was subjected to suction filtration, water was added to make the total amount 300 ml. 100 ml of banana extract (corresponding to 50 g of banana skin) and 100 ml of green tea extract (corresponding to 1 g of green tea) were mixed together and 2 g of citric acid was dissolved in the mixture. Then the mixture was heated at 95° C. for 3 hours. After cooled down, the solution was extracted with ethyl acetate 3 times to thereby obtain 0.312 g of ethyl acetate extracted product. In the same manner, banana extract liquid and green tea extract liquid were separately subjected to partitioning with ethyl acetate, to thereby obtain 0.015 g and 0.18 g of extracts of ethyl acetate respectively. The obtained extracts of ethyl acetate were analyzed by TLC (see TLC in FIG. 3). Due to the high molecular weight of proanthocyanidin in the banana skin extract, the extract is positive for vanillin hydrochloric acid reagent only at the origin point on the TLC analysis while in the product obtained by treating banana skin extract and green tea extract with citric acid, spots derived from new proanthocyanidin dimmer and trimer, which had not existed in the original extracts before the treatment, were observed.

Example 5

Astringent component contained in a large amount in astringent persimmon is proanthocyanidin having a very high molecular weight and constituted by four kinds of tea catechins (Tanaka et al., J. Chem. Soc. Perkin Trans 1, 1013-1022, 1994). 100 g of fresh immature persimmon fruit was pulverized together with 500 mL of 1% citric acid solution by using a whirling blender and further, 500 mL of 1% citric acid solution and 20 g of green tea were blended therein and the mixture was gently boiled for 3 hours. The reaction solution was subjected to suction filtration while it was hot, to thereby obtain 950 mL of filtrate. A half amount of the filtrate, 475 mL, was subjected to partitioning with ethyl acetate 4 times, to thereby obtain 2.56 g of ethyl acetate layer. The remaining half, 475 mL, was allowed to pass through a column of Sepabeads SP850 (200 mL) and after washed with water to thereby remove sugar, the adsorbed polyphenols were eluted out with 40-60% ethanol. The eluate was concentrated to thereby obtain 3.26 g of fraction containing catechin and proanthocyanidin. On the other hand, 200 g of immature persimmon fruit was pulverized together with 900 mL of acetone-water mixed solution (4:1, v/v) and subjected to extraction. Acetone was completely distilled off the filtrate and the obtained extract solution was allowed to pass through a column of Sepabeads SP850 (200 mL). As a result, Most of persimmon proanthocyanidins (persimmon tannin) was not adsorbed but eluted out only with water. The amount of polyphenol fraction adsorbed to the column and eluted out with aqueous alcohol was as small as 0.76 g. The molecular weight of proanthocyanidin in persimmon is assumed to be approximately $1.38 \times 10^4$ (Mastuo, T. et al., Agric. Biol. Chem., 42, 1637-1643, 1978), too large to come into pores of Sepabeads. On the other hand, persimmon proanthocyanidin treated with green tea, fractionated and reduced in the molecular weight, can come into pores of Sepabeads to be adsorbed. By the present Example, it was found out that Sepabeads could sift out proanthocyanidins having large molecular weights. The ethyl acetate extracted product obtained by treating persimmon with green tea and citric acid and the substance adsorbed to Sepabeads SP825 were compared with ethyl acetate extracted product of green tea and extract of aqueous acetone of immature persimmon by using TLC (see TLC in FIG. 4). With respect to the portion adsorbed to Sepabeads SP825, normal phase HPLC analysis was conducted and comparison was made with polyphenol fraction (containing catechin monomer, procyanidin dimer, trimer and tetramer and procyanidin having a higher molecular weight) obtained by separating hot water extracted product of Japanese cypress with DIAION HP20SS column chromatography (see HPLC in FIG. 5). The conditions of normal phase HPLC analysis were as follows.

column: LiChroCART Superspher Si 60 (4.6×250 mm),
column temperature: 28° C.,
mobile phase: hexane:methanol:tetrahydrofuran:trifluoroacetate (45:40:13.5:1.5),
flow rate: 1.0 mL/min,
detection: 254 nm As controls, (−)-epicatechin (monomer), procyanidin B4 (dimer), procyanidin C1 (trimer) and cinnamtannin A2 (tetramer) were used. These controls were separated from loquat seeds and identified by making comparison of $^1$H-NMR spectra with the values described in references. In HPLC, although a peak for caffeine was observed and besides it was conformed that polymers of up to four monomer molecules were present, it involved less peak-tailing thereafter as compared with proanthocyanidin of Japanese cypress.

Example 6

1 kg of fresh immature persimmon fruit was pulverized together with 2 L of water and the resultant was mixed with 200 g of green tea and 80 g of citric acid. Water was added to make the total amount 8 L and then the mixture was gently boiled for 3 hours. After heating, filtration was conducted while it was hot. The obtained filtrate was cooled down, allowed to pass through a column of Sepabeads SP825 and washed with water. The adsorbed portion was eluted out with aqueous ethanol, concentrated and then freeze-dried to obtain 59.0 g of a catechin-proanthocyanidin mixture. 6 g of the obtained mixture was allowed to pass through a column of Sephadex LH-20 to thereby fractionate it into eight fractions (Fr.) (see FIG. 6). The obtained amount of Fr.1, which mainly contained epicatechin and epigallocatechin, was 0.79 g. The obtained amount of Fr. 2, which mainly contained epicatechin 3-O-gallate, was 0.15 g. The obtained amount of Fr. 3, which mainly contained epigallocatechin 3-O-gallate, was 0.87 g. The obtained amount of Fr. 4, which was a mixture of epigallocatechin 3-O-gallate and proanthocyanidin dimmer, was 0.2 g. The obtained amounts of Fr.5 and Fr. 6 which both contained proanthocyanidin dimer, were 0.25 g and 0.51 g respectively. The obtained amount of Fr. 7, which mainly contained proanthocyanidin trimer, was 0.88 g. The obtained amount of Fr. 8, which contains the same trimer as Fr. 7 or proanthocyanidins having molecular weight higher than that, was 1.63 g. Among these fractions, Fr.5 and Fr.6 were purified with MCI-gel CHP20P column chromatography and Chromatorex ODS column chromatography (both using aqueous methanol as solvent) to thereby obtain 101.6 mg of (−)-epicatechin (4β→8)-(−)-epigallocatechin 3-O-gallate, 121.1 mg of (−)-epigallocatechin (4β→8)-(−)-epigallocatechin-3-O-gallate and 24.3 mg of (−)-epigallocatechin 3-O-gallate (4β→8)-(−)-epigallocatechin 3-O-gallate (see the following structural formulae). Besides, although many kinds of proanthocyanidin dimers were present, the inventors succeeded in pure separation of the above three types, identifying their structures by comparison of $^1$H-NMR spectra.

[Chem. 7]

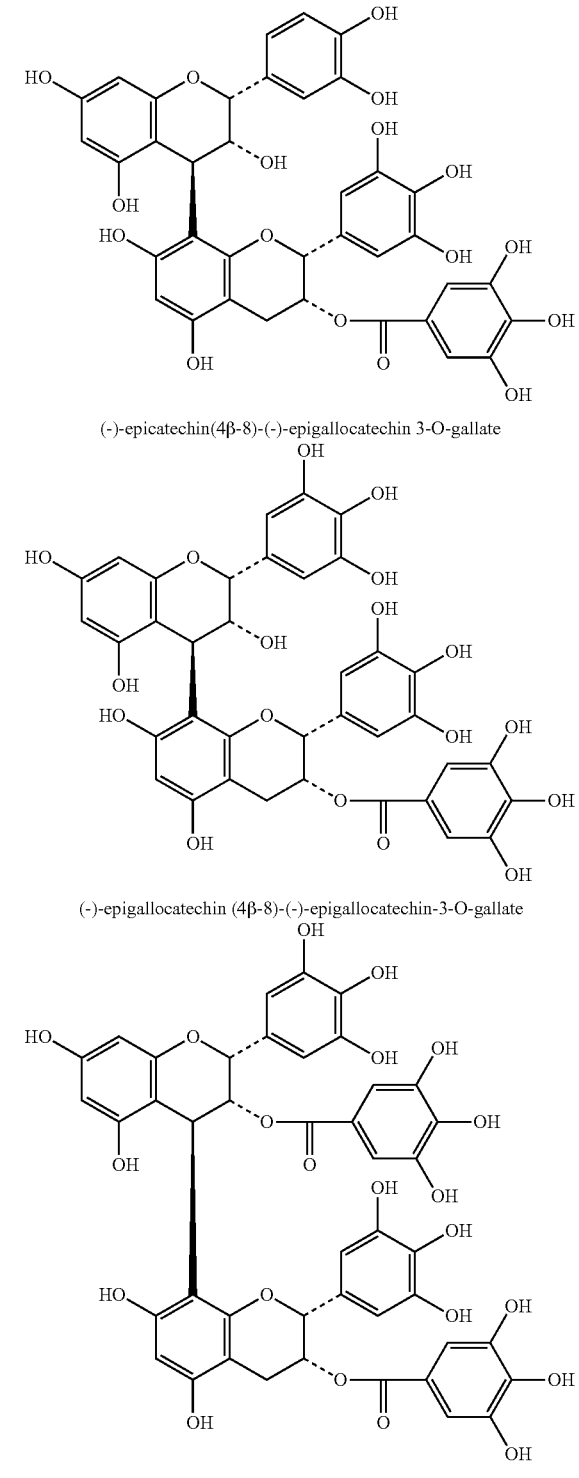

(−)-epicatechin(4β-8)-(−)-epigallocatechin 3-O-gallate (−)-epigallocatechin (4β-8)-(−)-epigallocatechin-3-O-gallate (−)-epigallocatechin-3-O-gallate (4β-8)-(−)-epigallocatechin-3-O-gallate Example 7

Production example of resveratrol-bonded compound 100 mg of grape seed polyphenol powder (Grape Seed P.E., products of Guilin Layn Natural Ingredients Corp., content of proanthocyanidins: 95% or more) and 120 mg of resveratrol, together with 100 mg of citric acid, dissolved in 10 mL of water, put into hot water for 3 hours (87 to 93° C.) to allow reaction to proceed, and the resultant was left standing to cool down to room temperature. With this liquid, a column of Sephadex LH-20 (inner diameter 2 cm, length 15 cm, about 50 mL, 70% methanol) was charged. 50 mL of 70% methanol and then 50 mL of 100% methanol were poured in sequentially to pass through the column, to thereby concentrate the fraction of the target substance. After freeze-drying treatment, 6.0 mg of a powder (hereinafter, abbreviate as Invention Substance A) was obtained.

This dry powder was dissolved in 1 mL of 70% methanol and with this solution, a column of MCI-gel CHP-20 (inner diameter 2 cm, length 15 cm about 50 mL) was charged. 50 mL of the same solvent was allowed to pass through the column to thereby concentrate the fraction of the target substance. After freeze-drying treatment, 2.4 mg of a powder was obtained. The obtained powder was subjected to HR-FAB-MS(High Resolution Fast Atom Bombardment Mass Spectrum) and $^1$H-NMR (hydrogen nuclear magnetic resonance spectrum, see Table 1). [M]$^+$ of the compound the obtained fraction mainly contained was observed at m/z: 516.1404 in HR-FAB-MS, which coincided with the value 516.1420 corresponding to a molecular formula $C_{29}H_{25}O_9$ with an error of 3.1 ppm. Therefore, the fraction was assumed to contain a compound represented by the molecular formula $C_{29}H_{25}O_9$, which led to a chemical structure where resveratrol bonded to catechin or epicatechin through carbon-carbon bond was considered.

In $^1$H-NMR (see Table 1) of the compound, in addition to the five proton signals on aromatic ring which are common in catechin and epicatechin, a group of signals having oxygen atoms at bases were observed at δ 5.04 (1H, br.s, 2-H) and δ 4.01 (1H, br.s, 3-H), which suggested presence of steric configuration of epicatechin. The signal at δ4.64 (1H, b r. s) was attributed to 4a-position of epicatechin part, and the resveratrol part was assumed to be located at 4b position. Besides, an envelope in 2H having the same shape as that of the signal observed at δ6.55 in phloroglucinol was observed, shifting to 0.56 ppm lower filed, showing that the newly formed c-c bond has a similar steric environment as well. In addition, the AB system on E-type conjugate double bond derived from a transstilbene structure of resveratrol (δ6.79, 6.97, each 1H, J=16.5 Hz), and A2B2 signal on the other aromatic ring (δ6.80, 7.36. each 2H, J=8.6 Hz) were observed. Based on the information, the chemical structure of the compound was assumed to be 4b-(4-resveratroyl)-(−)-epicatechin shown as follows.

[Chem. 8]

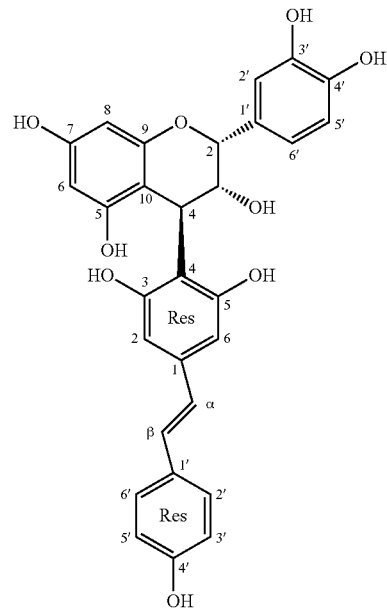

TABLE 1

$^1$H-NMR Signal Assignment of Invention Substance A (δ in ppm)

| H No. | |
|---|---|
| 2-H | 5.01 (br.s) |
| 3-H | 3.96 (br.s) |
| 4-H | 4.53 (br.s) |
| 6-H | 6.01 (d, J = 2.2 Hz) |
| 8-H | 5.98 (d, J = 2.2 Hz) |
| 2'-H | 6.96 (d, J = 1.7 Hz) |
| 5'-H | 6.74 (d, J = 8.3 Hz) |
| 6'-H | 6.67 (dd, J = 8.3, 1.7 Hz) |
| Ph 4-H | 5.99 (envelope) |
| 6-H | 5.99 (envelope) |

Note
1) Invention Substance was measured in acetone-d$_6$-D$_2$O.

Example 8

Production example of phloroglucinol-bonded compound Each 1.00 g of grape seed polyphenol and phloroglucinol were dissolved together with 500 mg of citric acid in 50 mL of water and the mixture was put in hot water (87 to 93° C.) for 3 hours. After the reaction, the resultant was left standing to cool down to room temperature. After a column of DIAION HP20 (inner diameter 3 cm, length 14 cm, about 100 ml) was charged with this solution, washing with about 300 ml of water was conducted. Then elution with about 200 ml of methanol was conducted, and the target fraction was concentrated and freeze-dried to obtain 1.24 g of a powder (hereinafter abbreviated as Invention Substance B).

Invention Substance B was dissolved in 5 ml of 70% methanol and a column of Sephadex LH-20 (inner diameter 3 cm, length 25 cm, about 180 ml) was charged with the solution. 500 ml of the same solvent was allowed to pass through the column, and the target fraction was concentrated and freeze-dried to thereby obtain 62.2 mg of a powder. The obtained powder was subjected to HR-FAB-MS and $^1$H-NMR analyses. With respect to the compound the obtained fraction mainly contained, [M]+ was observed at m/z: 414.0941, in HR-FAB-MS, which coincided with the calculation value 414.0950 corresponding to the molecular formula $O_{21}H_{18}O_9$, with an error margin of 2.2 ppm. (an error of 10 ppm or less is allowable). Accordingly, the compound was assumed to have a molecular formula of $O_{21}H_{18}O_9$, which suggested a chemical structure where phloroglucinol was bonded to catechin or epicatechin through carbon-carbon bond. In $^1$H-NMR of the compound (see Table 2), in addition to five proton signals on the aromatic ring common to catechin and epicatechin, a group of signals having oxygen atoms at the foot was observed at 5.01 (1H, br.s, 2-H) and 3.96 (1H, br.s, 3-H), suggesting that the compound had an epicatechin steric configuration. It was assumed that the proton signal of δ4.53 (1H. br.s) was attributable to 4 position of epicatechin part and that the phloroglucinol part was located at 4 position. Besides, a signal attributable to c-4 and c-6 derived from phloroglucinol in 2H was observed at δ5.99 as equivalent envelope, suggesting that the newly formed C—C bond generated a rotation barrier. Based on this information, the chemical structure of the compound was assumed to be 4-(2-phloroglucinol)-(−)-epicatechin as shown in the following formula. $^{13}$C-NMR (carbon-13 Nuclear Magnetic Resonance spectrum, see Table 3) on the compound supported the chemical structure.

[Chem. 9]

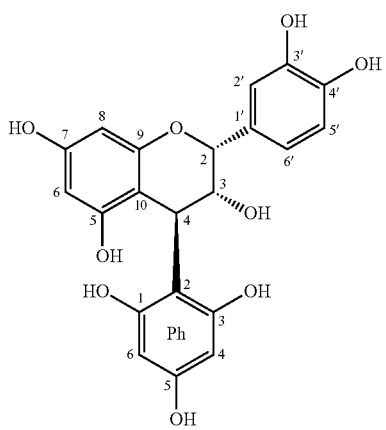

TABLE 2

$^1$H-NMR Signal assignment of Invention Substance B (δ in ppm)

| H No. | |
|---|---|
| 2-H | 5.04 (br.s) |
| 3-H | 4.01 (br.s) |
| 4-H | 4.64 (br.s) |

TABLE 2-continued $^1$H-NMR Signal assignment of Invention Substance B (δ in ppm)

| H No. | |
|---|---|
| 6-H | 6.00 (d, J = 2.2 Hz) |
| 8-H | 6.02 (d, J = 2.2 Hz) |
| 2'-H | 6.97 (d, J = 1.7 Hz) |
| 5'-H | 6.74 (d, J = 8.3 Hz) |
| 6'-H | 6.67 (dd, J = 8.3, 1.7 Hz) |
| Res 2 and 6-H | 6.55 (envelope) |
| α-H | 6.79 (d, J = 16.5 Hz)[a] |
| β-H | 6.97 (d, J = 16.5 Hz)[a] |
| 2' and 6'-H | 6.80 (d, J = 8.6 Hz)[c] |
| 3' and 5'-H | 7.36 (d, J = 8.6 Hz)[c] |

Note
1) Invention Substance B was measured in acetone-$d_6$-$D_2O$.
2) If the same letter is appended on right shoulders, the assignment may be exchanged with each other.

TABLE 3

$^{13}$C-NMR Signal Assignment of Invention Substance B (δ in ppm)

| C No. | | |
|---|---|---|
| C | -2 | 76.8 |
| | -3 | 72.3 |
| | -4 | 36.7 |
| | -5 | 157.7[a] |
| | -6 | 95.4 |
| | -7 | 158.4[b] |
| | -8 | 96 |
| | -9 | 158.5[b] |
| | -10 | 100.3 |
| | -1' | 132.2 |
| | -2' | 115 |
| | -3' | 145.0[c] |
| | -4' | 145.3[c] |
| | -5' | 115.1 |
| | -6' | 119 |
| Ph | -1 | 157.7[a] |
| | -2 | 100.3 |
| | -3 | 157.5[a] |
| | -4 | 106.6 |
| | -5 | 157.7[a] |
| | -6 | 106.6 |

Note
1) Invention Substance B was measured in acetone-$d_6$-$D_2O$.
2) If the same letter is appended on right shoulders, the assignment may be exchanged with each other.

Example 9

Production Example of Compound Having Grape Seed-Derived Epigallocatechin Gallate (EGCG) Bonded Thereto 5.00 g of grape seed polyphenol powder (Grape Seed P.E., LAYN, proanthocyanidin content 95%) was dispersed and dissolved in about 100 ml of water and then the solution was poured into a column of SEPABEADS SP850 (inner diameter 3.8 cm, length 20 cm, about 230 ml) and eluted with water. The obtained fraction was concentrated and freeze-dried to thereby obtain 2.44 g of a polymer powder (48.8%).

Each 1.00 g of the obtained grape seed polyphenol polymer powder and EGCG were dissolved together with 500 mg of citric acid in 50 ml of water and the vessel containing the mixture was put in hot water (87 to 93° C.) for three hours. After the reaction, it was left standing to cool down to room temperature. A column of DIAION HP20 (inner diameter 3 cm, length 14 cm, about 100 ml) was charged with this liquid and washing with about 300 ml water was conducted. The fraction obtained by eluting with about 200 ml of methanol was concentrated and freeze-dried to thereby obtain 1.85 g of a powder (hereinafter abbreviated as Invention Substance C).

Example 10

Production Example of Compound Having Myricae Cortex Polyphenol (EGCG Polymer) EGCG Bonded Thereto A piece of Wax myrtle (Myricaceae), a piece of *Myrica rubra* (Myricaceae) bark, that is, "Myricae Cortex", was immersed in cold 50% acetone of an amount of 5 to 10 times (W/V) of the piece for 3 to 7 days to thereby obtain a dark brown extract liquid. The obtained liquid was concentrated and yellow crystal of myricitrin (myricetin 3-O-α-L-rhamnopyranoside) was filtered out repeatedly by using filter paper. The obtained filtrate, after further concentration, was freeze-dried to thereby obtain a dark brown powder at a yield of 14% from resin piece. 14.0 g of this powder was dissolved in about 70 mL of 50% methanol and a column of Sephadex LH-20 (inner diameter 5 cm, length 20 cm, about 400 mL) was charged with the solution. After 1.5 L of the same solvent and then 0.7 L of 70% methanol were allowed to pass through the column, 1 L of 70% acetone were allowed to pass therethrough, to recover EGCG polymer fraction. The obtained fraction was concentrated and freeze-dried to obtain 9.37 g of an EGCG polymer powder (66.9%). Each 1 g of EGCG polymer derived from Myricae Cortex and EGCG was dissolved with 500 mg of citric acid in 50 mL of water and the vessel containing the mixture was put in hot water (87 to 93° C.) for 3 hours. After reaction, the resultant was left standing to cool down to room temperature. A column of DIAION HP20 (inner diameter 3 cm, length 14 cm, about 100 mL) was charged with this liquid, washing with about 300 mL of water was conducted. The fraction obtained by eluting with about 200 mL of methanol was concentrated and freeze-dried, to thereby obtain 1.85 g of a powder (hereinafter referred to as "Invention Substance D").

Example 11

Production Example of Persimmon-Skin-Derived Compound Having Tea Polyphenol Bonded Thereto 1.00 g of dry powder of persimmon skin and 300 mg of tea extract (PF-TP 90, manufactured by Pharma Foods International co., Ltd., tea polyphenol content: 90% or more, total content of catechin: 80% or more (with EGCG content of 50% or more) were dissolved with 500 mg of citric acid in 50 ml of water and the vessel containing the mixture was put in hot water (87 to 93° C.) for 3 hours. After reaction, the resultant was left standing to cool down to room temperature. After a column of SEPABEADS SP850 (inner diameter 3 cm, length 14 cm, about 100 ml) with this liquid, washing with about 300 ml of water was conducted and elution with about 200 ml of methanol was conducted. After a column of DIAION HP20 (inner diameter 3 cm, length 14 cm, about 100 ml) was charged with the obtained fraction, washing with about 300 ml of water was conducted. Then the fraction obtained by elution with about 200 ml of methanol was concentrated and freeze-dried to thereby obtain 464 mg of a powder (hereinafter referred to as "Invention Substance E").

Example 12

Production Example of Compound Having Litchee-Derived Polyphenol Epigallocatechin Gallate (EGCG) Bonded Thereto 5.00 g of litchee nut polyphenol powder (Litchi P.E., product of Guilin Layn Natural Ingredients Corp., proanthocyanidin content: 90% or more) was dispersed and dissolved in about 100 ml of water and a column of SEPABEADS SP850 (inner diameter 3.8 cm, length 20 cm, about 230 ml) was charged with the mixture. The fraction obtained by eluting with water was concentrated and freeze-dried to thereby obtain 3.02 g of a polymer powder (60.4%). Each 1.00 g of the obtained litchee nut polyphenol polymer powder and EGCG was dissolved with 500 mg of citric acid in 50 ml of water and the vessel containing the mixture was put in hot water (87 to 93° C.) for 3 hours. After reaction, the resultant was left standing to cool down to room temperature. After a column of DIAION HP20 (inner diameter 3 cm, length 14 cm, about 100 ml) was charged with this liquid, washing with about 300 ml of water was conducted. The fraction obtained by eluting with about 200 ml of water was concentrated and freeze-dried to thereby obtain 1.80 g of a powder (hereinafter referred to as Invention Substance F).

Test Example 1

With respect to Invention Substances A to E obtained in Examples 7 to 11 respectively, evaluation tests were conducted on antioxidative properties by measuring 1,1-diphenyl-2-picrylhydrazyl (DPPH) radical-scavenging activity and TEAC (Trolox Equivalent Antioxidant Capacity) method.

[DPPH Assay]
Procedures:

With respect to each sample, 1,1-diphenyl-2-picrylhydrazyl (DPPH) radical-scavenging activity was evaluated as follows. In a 96-hole microplate, 100 μL of DPPH solution (60 μM ethanol solution) was placed. Added thereto was 100 μL of ethanol solution of test sample or 100 μL of ethanol as control, and the mixture was gently mixed together and left standing at room temperature for 30 minutes. Then, absorbance at 520 nm was measured. The DPPH radical-scavenging activity was calculated by the following formula and 50% effective concentration (EC50) was calculated from The DPPH radical-scavenging activity value of test sample gradually diluted and its concentration.

DPPH radical-scavenging activity(%)=(1-absorbance of test sample)/absorbance of control×100    [Formula 1]

As substance to be compared with Invention Substance A, epicatechin (EP) and resveratrol (RS) were used. As substance to be compared with Invention Substance B, epicatechin and phloroglucinol (PL) were used. As substance to be compared with Invention Substances C to E, grape seed polyphenol polymer (GP) was used. The measurement results are shown in FIGS. 7 to 9, together with data of compared substances.

In epicatechin, DPPH activity of 48.7% was acknowledged while in resveratrol, the activity was only 23.1%. In Invention Substance A where epicatechin and resveratrol were combined with each other, the activity was as high as 76.1%, which was significantly excellent (FIG. 7).

In epicatechin, DPPH activity of 43.0% was observed while in phloroglucinol, little such activity was observed.

Invention Substance B where phloroglucinol was combined with epicatechin showed significantly high scavenging activity as compared with both of the substances (FIG. 8).

Further, Invention Substances C (41.3%) and D (35.1%) showed higher scavenging activities than the compared substances did (26.9%). The scavenging activity Invention Substance E (26.8%) showed was equivalent to that of the compared substances (FIG. 9). [TEAC].

Method:

TEAC (Trolox Equivalent Antioxidant Capacity) method is a method of relatively evaluating antioxidative strength by converting antioxidative activity of a compound into antioxidative activity of Trolox which is a α-tocopherol derivative and the method is widely employed as an index of antioxidative activity.

To 36 μL of 70 μM metmyoglobin solution, 300 μL of ABTS solution and 487 μM←L? of 5 mM phosphate buffered saline were added. Subsequently, sample solution or 1.25 mM Yrolox solution was added thereto and gently mixed together for 5 minutes at 0° C. After 167 μL of 450 μM hydrogen peroxide solution was added thereto and mixed for 10 seconds, reaction was allowed to proceed for 5 minutes at room temperature. Absorbance at 734 nm was measured and the absorbance ratio between the sample and the Trolox solution was calculated to serve as TEAC value of the sample against 1.00 mm Trolox.

As in the above-described DPPH assay, as substance to be compared with Invention Substance A, epicatechin and resveratrol were used and as substance to be compared with Invention Substance B, epicatechin and phloroglucinol were used. As substance to be compared with Invention Substances C to E, grape seed polyphenol polymer was used.

The measurement results are shown in FIGS. 10 to 12, together with data of compared substances.

In epicatechin, TEAC activity of 1.2 mM was observed while in resveratrol, the activity was only 1.11 mM. In Invention Substance A where epicatechin and resveratrol were combined with each other, the activity was 1.33 mM, which was significantly high (FIG. 10). In phloroglucinol, TEAC activity was as low as 0.52 mM while in Invention Substance B where epicatechin was combined with phloroglucinol, the activity was 1.44 mm, which was significantly higher than the two when alone (FIG. 11).

Invention Substances C (1.11), D (1.11) and E (0.97) showed high TEAC values as compared with the compared substance (0.73) (FIG. 12).

Test Example 2

As substance to be compared with Invention Substance F obtained in Example 12, litchee nut polyphenol (LP) and tea extract were used to conduct comparative experiment.

[In Vitro Test]

Test Method:

NIH3T3 cells were seeded on a 96-hole plate and cultivated overnight at 37° C. On the next day, the medium was changed to a serum-free culture medium and the substance to be tested was added thereto and further cultivation is conducted for an hour. Then, UV was irradiated for 20 minutes. The medium was changed to a serum-containing medium and cultivation was conducted overnight at 37° C. Cell viability was evaluated by MTT method. The cell in the medium without addition of the substance to be tested was used as control group (C).

The results are shown in FIG. 13. In the control group, the cell viability against UV irradiation was about 20% while in Invention Substance F, the viability was the highest, which showed that Invention Substance F, significantly reducing the number of cell deaths as compared with the compared substance, had UV protection effect.

[In Vivo Test]

Test Method:

To Slc:ddY male mice of 9 weeks old, Invention Substance F, LP and TE were forcibly orally administered respectively each in an amount of 50 mg/kg body weight every day for 3 weeks. To a control group of mice (C), the same amount of water was administered. Two hours after administration of the test substance on the final day, the TEAC antioxidative activity and the amount of lipid peroxide in the serum were measured by collecting blood from the heart under ether anesthesia. The TEAC measurement was conducted in the above-described manner. The lipid peroxide amount was measured by using a commercially available kit (lipid peroxide-Test Wako, manufactured by Wako Pure Chemical Industries, Ltd.) and measuring fluorescence at excitation wavelength 515 nm and fluorescent wavelength 553 nm in reaction between precipitation of lipid peroxide and 2-thiobarbituric acid reagent in phosphotungstic acid solution under the acidic condition of sulfuric acid.

The results are shown in FIGS. 14 and 15. Invention Substance F showed significantly high antioxidative activity as compared with the compared substance and the control group. Also, the amount of lipid peroxide in the serum was significantly low as compared with the case using the compared substance.

[In Vivo Test]

Test Method:

To Slc:ddY male mice of 6 weeks old, Invention Substance F, LP and TE were forcibly orally administered respectively each in an amount of 50 mg/kg body weight every day for 3 weeks. To a control group of mice (C), the same amount of water was administered.

On the day before dissection, 2-NP (70 mg/kg body weight) was intraperitoneally administered and 24 hours later, collection of blood from the heart was conducted under ether anesthesia to thereby measure GOT and GPT in the serum. Further, the liver was isolated to measure the lipid peroxide amount in the organ.

The results are shown in FIGS. 16 and 17. Due to administration of 2-NP, disorder was caused to the liver, which resulted in increasing GOT and GPT concentrations. However, Invention Substance F significantly reduced such increases as compared with the control group and the compared substance. Moreover, the amount of lipid peroxide in the liver was significantly low as compared with the case using the compared substance.

BRIEF DESCRIPTION OF DRAWINGS

FIG. 1(A) is an HPLC chromatogram on Example 3 treating Japanese cypress bark and green tea with heat under an acidic condition. FIGS. 1(B) and (C) are HPLC chromatograms on Example 3 treating Japanese cypress bark (FIG. 1(B)) and green tea (FIG. 1(C)) each independently with heat under an acidic condition, respectively.

FIG. 2 is a TLC photograph showing that new proanthocyanidins which had not been present in raw material Japanese cypress bark and green tea were generated by heat treating the materials with heat in Example 4. In the Figure, A is the result on ethyl acetate layer of green tea after treatment, B is the result on ethyl acetate layer of Japanese cypress bark after treatment, and C is the result on ethyl acetate layer of Japanese cypress bark and green tea after treatment. Spot M is derived from Non-galloylated monomer, MG is derived from galloylated proanthocyanidin monomer, D is derived mainly from galloylated proanthocyanidin dimer and T is derived mainly from galloylated proanthocyanidin trimer.

FIG. 7 shows the DPPH radical-scavenging activity of Invention Substance A obtained in Example 7.

FIG. 8 shows the DPPH radical-scavenging activity of Invention Substance B obtained in Example 8.

FIG. 9 shows the DPPH radical-scavenging activity of Invention Substances C to E obtained in Examples 9-11.

FIG. 10 shows the results of evaluation by TEAC method on antioxidative ability of Invention Substance A obtained in Example 7.

FIG. 11 shows the results of evaluation by TEAC method on antioxidative ability of Invention Substance B obtained in Example 8.

FIG. 14 shows the results of evaluation by TEAC method on antioxidative ability of Invention Substance F obtained in Example 12.

FIG. 15 shows measurement results of the LPO level in the serum in the antioxidative ability test on Invention Substance F obtained in Example 12.

Figure 3:
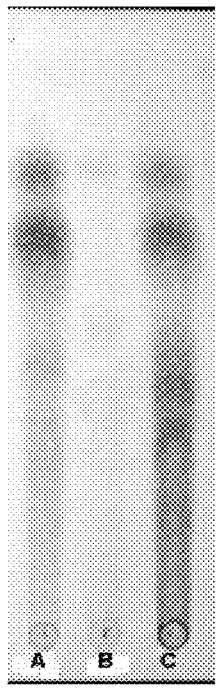
FIG. 3 is a TLC photograph showing that new proanthocyanidins which had not been present in raw material banana skin extract and green tea were generated by heat treating the materials with heat in Example 6. In the Figure, A is the result on ethyl acetate layer of green tea alone after treatment, B is the result on ethyl acetate layer of banana skin extract alone after treatment, and C is the result on ethyl acetate layer of banana skin extract and green tea after treatment.
Figure 4:
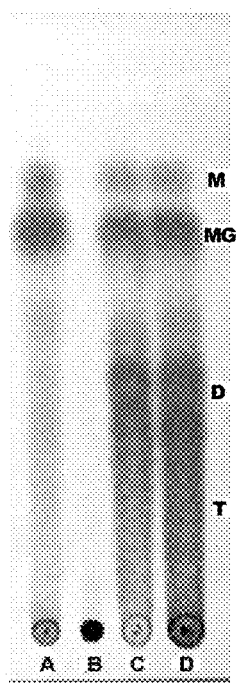
FIG. 4 is a TLC photograph showing that new proanthocyanidins which had not been present in raw material immature persimmon fruit and green tea were generated by heat treating the materials with heat in Example 5. In the Figure, A is the result on ethyl acetate layer of green tea alone after treatment, B is the result on ethyl acetate layer of immature persimmon fruit alone after treatment, C is the result on ethyl acetate layer of immature persimmon fruit and green tea after treatment and D is the result of the product obtained by allowing the resultant (extract liquid) obtained by treating the immature persimmon fruit and green tea to pass through Sepabead 825 and eluting the adsorbed portion with water-ethanol. Spots M, MG, D and T are the same as in FIG. 2.
Figure 5A:
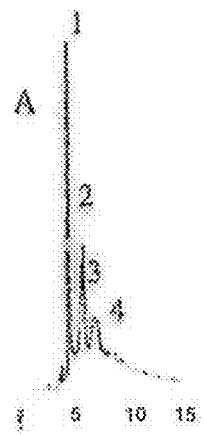
FIG. 5(A) is the results of normal-phase HLPC analysis on the product obtained after allowing the resultant (extract liquid) obtained by treating the immature persimmon fruit and green tea to pass through Sepabead 825 and then eluting the adsorbed portion with water-ethanol in Example 5.
Figure 5B:
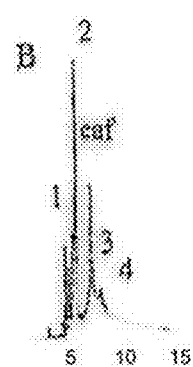
FIG. 5(B) is the results of normal-phase HLPC analysis on the Japanese cypress proanthocyanidin used as comparative example.
Figure 6:
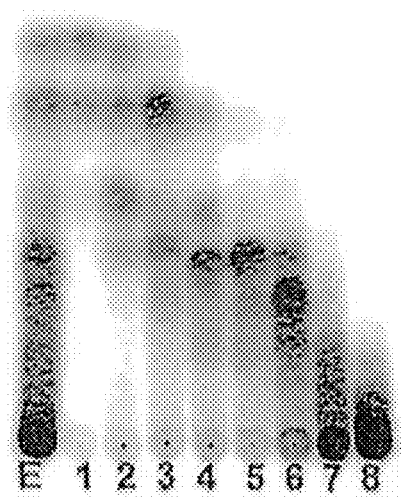
FIG. 6 shows the result of TLC analysis on fractions (Fr 1 to Fr 8) obtained by treating immature persimmon fruit and green tea with heat under acidic condition and then allowing the obtained catechins and proanthocyanidins to pass through Sephadex LH-20 column chromatography and on a mixture (E) before the separation in Example 6.
Figure 12:
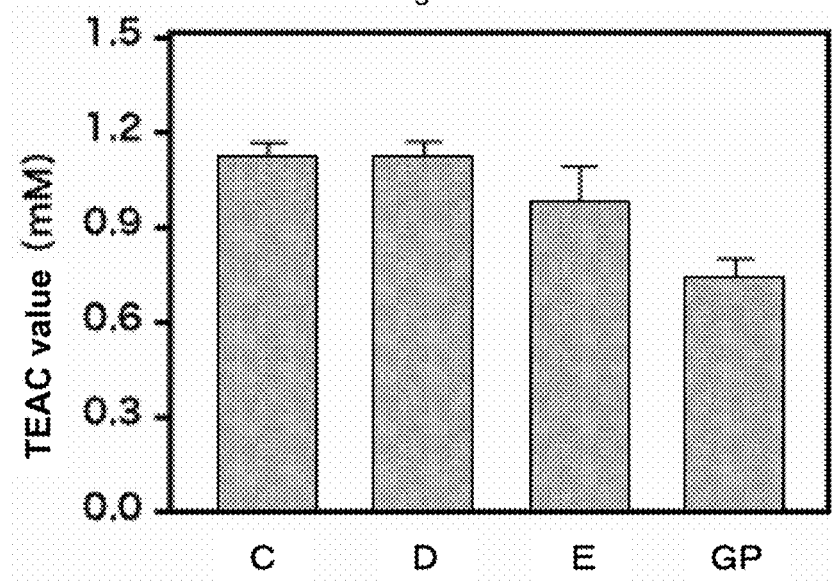
FIG. 12 shows the results of evaluation by TEAC method on antioxidative ability of Invention Substances C to E obtained in Examples 9 to 11.
Figure 13:
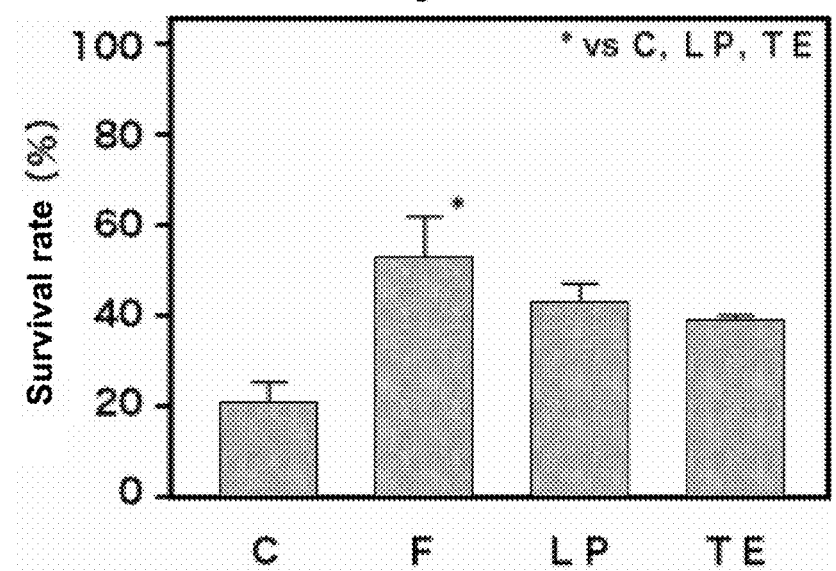
FIG. 13 shows the results of UV-protection effect test on Invention Substance F obtained in Example 12.
Figure 16:
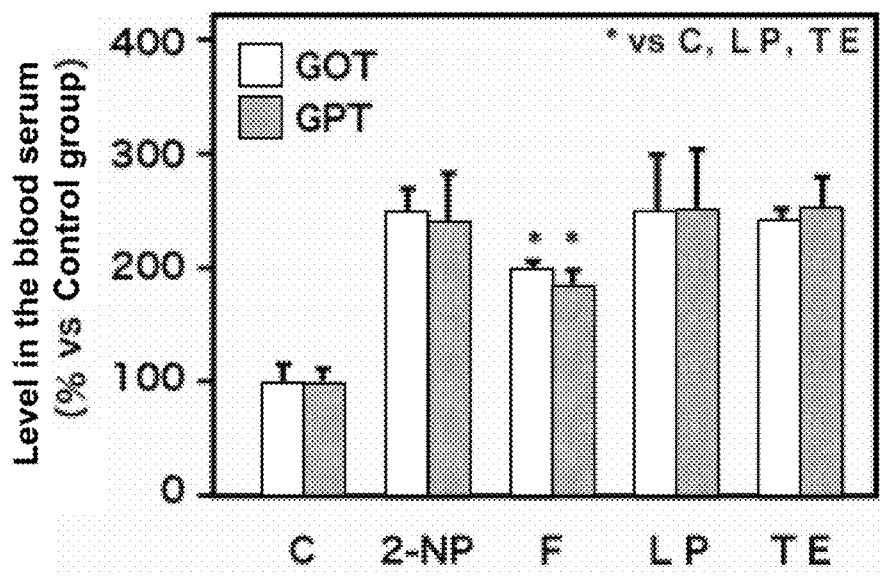
FIG. 16 shows measurement results of the GOT and GPT levels in the serum in the antioxidative ability test on Invention Substance F obtained in Example 12.
Figure 17:
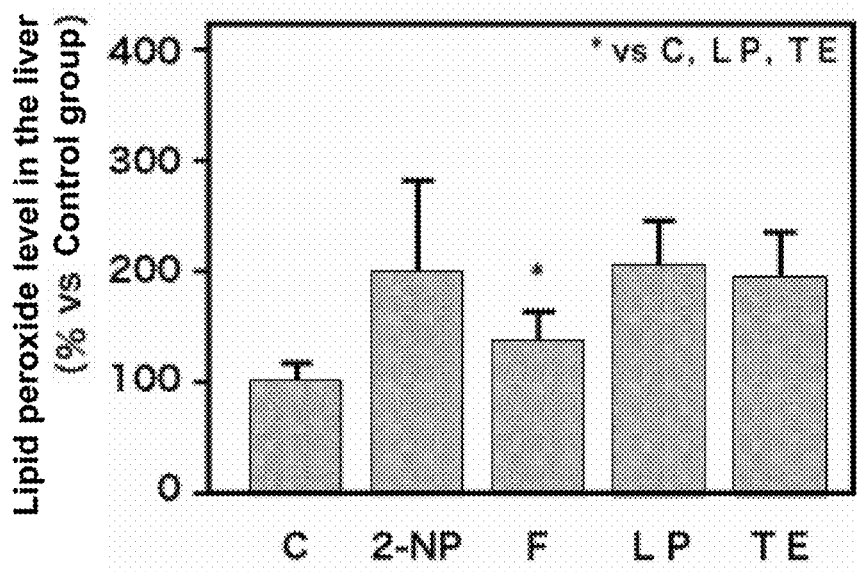
FIG. 17 shows measurement results of the LPO level in the liver in the antioxidative ability test on Invention Substance F obtained in Example 12.

What is claimed is:

1. A method for producing a composition having a main component of proanthocyanidin oligomers, the method comprising steps of:
   heating a material containing a proanthocyanidin polymer in an acidic aqueous solution with at least one of: green tea, green tea extract and epigallocatechin gallate (EGCG) to form a reaction solution including the proanthocyanidin oligomers reduced in molecular weight relative to the proanthocyanidin polymer and having catechins or EGCG bonded to terminals thereof, the reaction solution having an acid concentration of 0.1 to 1.0 N;
   concentrating the reaction solution to form a concentrated solution; and
   performing at least one of the following operations on the concentrated solution: drying and a fractionating treatment.

2. The method of claim 1, where the material containing the proanthocyanidin polymer is a plant material.

3. The method of claim 2, wherein the plant material is selected from at least one of: grape, pine, *Chamaecyparis obtuse*, camphor tree, wax myrtle, cacao, date plum, banana, Chinese quince, apple, hawthorn, litchee, *Myrica rubra* and Cinnamoni Cortex.

4. The method of claim 1, wherein the acidic aqueous solution is formed with an inorganic acid.

5. The method of claim 1, wherein the acidic aqueous solution is formed with an organic acid.

6. The method of claim 1, wherein the acidic aqueous solution is formed with both an inorganic acid and an organic acid.

7. The method of claim 1, wherein the acidic aqueous solution is formed with at least one of: hydrochloric acid, sulfuric acid, nitric acid, acetic acid, citric acid, ascorbic acid and malic acid.

8. The method of claim 1, wherein the proanthocyanidin oligomers of the composition have a polymerization degree of 2 to 4.

9. The method of claim 1, wherein the step of heating the proanthocyanidin polymer in the acidic aqueous solution with the at least one of:
   green tea, green tea extract and EGCG is performed at a temperature of 90 to 100 degrees Celsius for 1 to 4 hours.

10. A method for producing a composition having a main component of proanthocyanidin oligomers, the method comprising steps of:
    heating a material containing a proanthocyanidin polymer in an acidic aqueous solution with at least one of: green tea, green tea extract and epigallocatechin gallate (EGCG) to form a reaction solution including the proanthocyanidin oligomers reduced in molecular weight relative to the proanthocyanidin polymer and having catechins or EGCG bonded to terminals thereof;
    concentrating the reaction solution to form a concentrated solution; and
    performing at least one of the following operations on the concentrated solution: drying and a fractionating treatment;
    wherein the acidic aqueous solution is formed with an inorganic acid.

11. The method of claim 10, wherein the acidic aqueous solution is also formed with an organic acid.

\* \* \* \* \*